(12) United States Patent
Tice, Jr. et al.

(10) Patent No.: US 6,312,930 B1
(45) Date of Patent: Nov. 6, 2001

(54) METHOD FOR DETECTING BACTERIA USING PCR

(75) Inventors: George Tice, Jr., Penns Grove, NJ (US); William Mark Barbour, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 08/929,713

(22) Filed: Sep. 15, 1997

Related U.S. Application Data

(63) Continuation-in-part of application No. 08/714,718, filed on Sep. 16, 1996, now abandoned.

(51) Int. Cl.[7] .......................... C07H 19/00; C07H 21/04; C07H 21/00; C12P 19/34
(52) U.S. Cl. ...................... 435/91.2; 536/22.1; 536/24.3; 536/25.32; 424/408
(58) Field of Search .................... 435/91.2; 536/22.1, 536/24.3, 25.32; 424/408

(56) References Cited

U.S. PATENT DOCUMENTS

| | | | |
|---|---|---|---|
| 3,932,943 | 1/1976 | Briggs et al. | 34/5 |
| 4,678,812 | 7/1987 | Bollin, Jr. et al. | 514/777 |
| 4,683,202 | 7/1987 | Mullis | 435/91 |
| 4,762,857 | 8/1988 | Bollin, Jr. et al. | 514/777 |
| 5,307,640 | 5/1994 | Fawzy et al. | 62/52.1 |
| 5,321,130 | 6/1994 | Yue et al. | 536/23.1 |
| 5,436,134 | 7/1995 | Haugland et al. | 435/34 |
| 5,475,984 | 12/1995 | Fermani et al. | 62/64 |
| 5,523,205 | 6/1996 | Cossart et al. | 435/6 |
| 5,534,416 | 7/1996 | Millard et al. | 436/34 |
| 5,563,037 | 10/1996 | Sutherland et al. | 435/6 |
| 5,658,751 | 8/1997 | Yue et al. | 435/34 |
| B1 4,683,195 | 7/1987 | Mullis et al. | 435/6 |

FOREIGN PATENT DOCUMENTS

| | | | |
|---|---|---|---|
| 2102963 | 11/1993 | (CA) . | |
| 576 842 A2 | 1/1994 | (EP) . | |
| 0 586 112 A2 | 3/1994 | (EP) | C12N/15/11 |
| 5-219997 | 8/1993 | (JP) . | |
| WO 93/11264 | 6/1993 | (WO) | C12Q/1/68 |
| WO 94/25595 | 11/1994 | (WO) | C12N/15/31 |
| WO 94/25597 | 11/1994 | (WO) | C12N/15/31 |
| WO 95/00664 | 1/1995 | (WO) | C12Q/1/68 |

OTHER PUBLICATIONS

John G.K. Williams et al., DNA Polymorphisms Amplified by Arbitrary Primers are Useful as Genetic Markers, *Nucleic Acids Research*, 18(22), 6531–6535, 1990.
John Welsh et al., Fingerprinting Genomes Using PCR with Arbitrary Primers, *Nucleic Acids Research*, 18(24), 7213–7218, 1990.
Southern, E.M. et al., Pulsed Field Gel Electrophoresis, 1–19, 1995.
Samapour, *J. Clin. Microbiol.*, 33(8), 2150–2154, 1995.
Srinivasan et al., *Appl. Theor. Electrophor.*, 3(5), 235–239, 1993.
Axton et al., Molecular Cell Probes, 8(3), 245–250, 1994.
Sailer et al., *Cytometery*, 25(2), 164–172, 1996.
Ramotar et al., *J. Clin. Microbiol.*, 33(8), 2188–2191, 1995.
Ursi et al. Utility of an internal control for the polymerase chain reaction, APMIS, vol. 100, pp. 635–639, 1992.*

* cited by examiner

*Primary Examiner*—Ardin H. Marschel
*Assistant Examiner*—Joyce Tung

(57) ABSTRACT

The present invention is a method for the detection of a specific target bacteria in a complex sample mixture. The sample mixture may contain a variety of components including non-target or background microorganisms as well as other organic contaminants such as food debris. The method proceeds by first culturing the complex sample mixture in a non-selective growth medium, followed by isolation and detection of target bacteria DNA. Target DNA is detected via a DNA amplification protocol with a primer pair selected to amplify a specific, identifying portion of the target bacteria DNA. A control DNA is amplified concurrently with the target bacteria target DNA. The control DNA is specifically designed to be amplified with a single primer that is identical to one of the primers used in the amplification of the target genomic DNA. Use of this control validates the amplification reaction. Detection of the amplified target DNA and the control is accomplished by gel electrophoresis or by fluorescent means. The present method is particularly useful when carried out in a homogeneous format where fluorescence emissions from dyes, incorporated in the amplification products, may be detected without the separation of products from primers or DNA templates.

18 Claims, 16 Drawing Sheets

35 PRIMER

```
         TAGCCGGGACGCTTAATGCGGTTAACGCCATGCCGACACCAGCCCCGCCAGCGTGCCGA
     1   ----+----+----+----+----+----+----+----+----+----+----+----   60
         ATCGGCCCTGCGAATTACGCCAATTGCGGTACGGCTGTGGTCGGGCGGTCGCACGGCT
    5'-TAGCCGGGACGCTTAATGCGGTTAAC-3'

AACTGTAGAAACCATGCATCGGCAGAACGGTTTATTCAGCTCGCGTTCGACCGCCG
    61   ----+----+----+----+----+----+----+----+----+----+----+----  120
         TTGACATCTTTGGTACGTAGTAGCCGTCTTGCCAAATAAGTCGAGCGCAAGCTGGCGGC

CGCCTTCGACATTAATCGCCACTTCGGCGGCGCAAAACTGGCGCGAAAACGGCTAATC
   121   ----+----+----+----+----+----+----+----+----+----+----+----  180
         GCGGAAGCTGTAATTAGCGGTGAAGCCGCCGCGTTTTGACCGCGCTTTTGCCGATTAG

CAAGGGCAAAATCAGCGCGAGGCGACCACAGCGCGCTAAGAATAACCATCCCGG
   181   ----+----+----+----+----+----+----+----+----+----+----+----  240
         GTTCCCGTTTTAGTCGCGCTCCGCGCTGGTGTCGCGCGATTCTTATTGGTAGGGCC

TTACTGCACAGGTCATCGTCGTGCGAATAACCTTCGGGTGCCAAATCGTTTCACCAGCC
   241   ----+----+----+----+----+----+----+----+----+----+----+----  300
         AATGACGTGTCCAGTAGCAGCACGCTTATTGGAAGCCCACGGTTTAGCAAAGTGGTCGG
```

FIG. 1a

```
241 TTACTGCACAGGTCATCGTCGTGCGAATAACCTTCCGGTGCCAAATCGTTCACCAGCC
    ----------+---------+---------+---------+---------+---------+ 300
    AATGACGTGTCCAGTAGCAGCACGCTTATTGGAAGGCCACGGTTTAGCAAAGTGGTCGG

301 AGGCGGAACAAAGAATACCGCTCATTGAACCGATAGAAAGCCCGAATAAGACCGCCCCA
    ----------+---------+---------+---------+---------+---------+ 360
    TCCGCCTTGTTTCTTATGGCGAGTAACTTGGCTATCTTTCGGGCTTATTCTGGCGGGGT

361 TTTCCGCGGTAGAGACGGAAAGAATATCCCGAATAGCAGGCGTTCGGGTTGCCCAGGAGG
    ----------+---------+---------+---------+---------+---------+ 420
    AAAGGCGCCATCTCTGCCTTTCTTATAGGGCTTATCGTCCGCAAGCCCAACGGGTCCTCC

421 CCATCAGCAGTCCGGGTAAAAGAAGAACATAAACAGGCCCAGGTACGGCGTTTTAAGG
    ----------+---------+---------+---------+---------+---------+ 480
    GGTAGTCGTCAGGCCCATTTTCTTCTTGTATTTGTCGGGTCCATGCCGCAAAATTCC

481 CGTTACGTGAGGAGGACGGTCATAGCGTCAGGCCAGAAATAGAAGCGAGAGGTAAAC
    ----------+---------+---------+---------+---------+---------+ 540
    GCAATGCACTCCTCCTCCTGCCAGTATGCGAGTCCGTCTTTTATCTTCGCTCTCCATTTG

541 ATTAGCAAGCTTGTGTACATTTGTACATATCATCGTCATACTTCATTGTGCAGACAGTTT
    ----------+---------+---------+---------+---------+---------+ 600
    TAATCGTTCGAACACATGTAAACATGTATAGTAGCAGTATGAAGTAACACGTCTGTCAAA
```

FIG. 1b

```
601  TTACTGTCTGTGTTTTTCAGGCGTAAGCGGCAGGCTACTATCGCCTGCATCCTGAATGAGAT
     ------+---------+---------+---------+---------+---------+   660
     AATGACAGACAAAAAGTCGCATTCGCCGTCCGATGATAGCGGACTAGGACTTACTCTA

661  GTGGAACTCATCATGAAAGAAAATGCCGTAAGCGGCCAATGATCCTAAGCGACGGGAAA
     ------+---------+---------+---------+---------+---------+   720
     CACCTTGAGTAGTACTTTCTTTTACGGCATTCGCCGGTTACTAGGATTCGCTGCCCTTT

3'-AAGTCCGGTGTGACCTTCGCCATTTC-5'
                     AAATAATTCAGGCCACACTGGAAGCGGTAAAG
721  ------+---------+---------+                                 752
     TTTATTAAGTCCGGTGTGACCTTCGCCATTTC
                     761 PRIMER
```

FIG. 1C

```
                      761 PRIMER
           CTTTACCGCTTCCAGTGTGGCCTGAAAACGCCATGCCGACACCAGGCCCGCCAGCGTGC
    1      ------------------------------------------------------------  60
           GAAATGGCGAAGGTCACACCGGACTTTTGCGGTACGGCTGTGGTCGCGGGCGGTCGCACG
           5'-CTTTACCGCTTCCAGTGTGGCCTGAA-3'

CGAAACTGTAGAAACCATGCATCATCGGCAGAAACGGTTTTATTCAGCTCGCGTTCGACCG
    61     ------------------------------------------------------------ 120
           GCTTTGACATCTTTGGTACGTAGTAGCCGTCTTGCCAAATAAGTCGAGCGCAAGCTGGC

CCGGCGCCTTCGACATTAATCGCCACTTCGGGCGCCAAAACTGGCGCCGAAAACGGCTA
    121    ------------------------------------------------------------ 180
           GGCGCGAAGCTGTAATTAGCGGTGAAGCCCGCGGTTTTGACCGCGGCTTTTGCCGAT

ATCCAAGGGCAAAAATCAGCGCGAGGCGCACCACAGCGCGACGCTAAGAATAACCATCC
    181    ------------------------------------------------------------ 240
           TAGGTTCCCGTTTTTAGTCGCGCTCCGCGTGGTCGTCGCGCTGCGATTCTTATTGGTAGG

CGGTTACTGCCACAGTCATCGTCGTGCGAATAACCTTCCGGGTGCCAAATCGTTTCACCA
    241    ------------------------------------------------------------ 300
           GCCAATGACGGTGTCCAGTAGCAGCACGCTTATTGGAAGGCCCACGGTTTAGCAAAGTGGT
```

FIG. 2a

```
301  GCCAGGGCGAACAAAGAATACCGCTCATTGAACCGATAGAAAGCCCGAATAAGACCGCCC
     ------+---------+---------+---------+---------+---------+  360
     CGGTCCCGCCTTGTTTCTTATGGCGAGTAACTTGGCTATCTTTCGGGCTTATTCTGGCGGG

361  CCATTTCCGCGGTAGAGACGGAAAGAATATCCCGAATAGCAGGCGTTCGGGTTGCCCAGG
     ------+---------+---------+---------+---------+---------+  420
     GGTAAAGGCGCCATCTCTGCCTTTCTTATAGGGCTTATCGTCCGCAAGCCCAACGGGTCC

421  AGGCCATCAGCAGTCCGGGTAAAAAGAAGAACATAAACAGCGCCAGTACGGCGTTTTA
     ------+---------+---------+---------+---------+---------+  480
     TCCGGTAGTCGTCAGGCCCATTTTTCTTCTTGTATTTGTCGCGGTCCATGCCGCAAAAT

481  AGGGCGTTACGTGAGGAGGACGGTCATAGCGTCAGGCCAGAAAATAGAAGCGAGAGTA
     ------+---------+---------+---------+---------+---------+  540
     TCCGCAATGCACTCCTCCTGCCAGTATCGCAGTCCGGTCTTTTATCTTCGCTCTCCAT

541  AACATTAGCAAGCTTGTGTACATTTGTACATATCATCGTCATACTTCATTGTGCAGACAG
     ------+---------+---------+---------+---------+---------+  600
     TTGTAATCGTTCGAACACATGTAAACATGTATAGTAGCAGTATGAAGTAACACGTCTGTC
```

FIG. 2b

```
601 TTTTTACTGTCTGTTTTTCAGCGTAAGCGGCAGGCTACTATCGCCTGCATCCTGAATGA
    ------+---------+---------+---------+---------+---------+  660
    AAAAATGACAGACAAAAAGTCGCATTCGCCGTCCGATGATAGCGGACGTAGGACTTACT

661 GATGTGGAACTCATCATGAAAGAAAATGCCGTAAGCGCGCCAATGATCCTAAGCGACGGG
    ------+---------+---------+---------+---------+---------+  720
    CTACACCTTGAGTAGTACTTTCTTTTACGGCATTCGCGCGGTTACTAGGATTCGCTGCCC

3'-AAGTCCGGTGTGACCTTCGCCATTTC-5'
                                              755
721 AAAAATAATTCAGGCCACACTGGAAGCGGTAAAG
    ------+---------+---------+------
    TTTTTTATTAAGTCCGGTGTGACCTTCGCCATTTC
                        ‾‾‾‾‾‾‾‾‾‾‾‾‾‾‾‾‾‾‾‾‾‾‾‾‾‾
                        761 PRIMER
```

FIG. 2c

```
                         35 PRIMER                                          761 PRIMER

TAGCCGGGACGCTTAATGCGGTTCTTTACCGCTTCCAGTGTGGCCTGAAAACGCCATGCC           60
     ----+----+----+----+----+----+----+----+----+----+----+----+
     ATCGGCCCTGCGAATTACGCCAAGAAATGGCGAAGGTCACACCGGACTTTGCGGTACGG
  1  5'--TAGCCGGGACGCTTAATGCGGTTAAC-3'    CTTTACCGCTTCCAGTGTGGCCTGAA-3'

GACACCAGCGCCCGCCAGCGTGCCGAAACTGTAGAAACCATGCATCATCGGCAGAACGGT          120
     ----+----+----+----+----+----+----+----+----+----+----+----+
     CTGTGGTCGCGGGCGGTCGCACGGCTTTGACATCTTTGGTACGTAGTAGCCGTCTTGCCA
 61

TTTATTCAGCTCGCGGTTCGACCGCCCTTCGACATTAATCGCCACTTCGGCGGCGCC            180
     ----+----+----+----+----+----+----+----+----+----+----+----+
     AAATAAGTCGAGCGCCAAGCTGGCGGGAAGCTGTAATTAGCGGTGAAGCCGCCGCGG
121

AAAACTGGGCGCCGAAAACGCTAATCCAAGGGCAAAAATCAGGGCGAGGCGCACCACAG          240
     ----+----+----+----+----+----+----+----+----+----+----+----+
     TTTTGACCCGCGGCTTTTGCGATTAGGTTCCCGTTTTTAGTCCCGCTCCGCGGTGGTGTC
181

CGCGACGCTAAGAATAACCATCCCGGTTACTGCACAGGTCATCGTCGTGCGAATAACCTT         300
     ----+----+----+----+----+----+----+----+----+----+----+----+
     GCGCTGCGATTCTTATTGGTAGGGCCAATGACGTGTCCAGTAGCAGCACGCTTATTGGAA
241
```

FIG. 3a

```
301  CCGGGTGCCAAATCGTTTCACCAGCCGGAACAAAGAATACCGCTCATTGAACCGAT
     ----+----|----+----|----+----|----+----|----+----|----+----|  360
     GGCCCACGGTTTAGCAAAGTGGTCGGCCCTTGTTTCTTATGGCGAGTAACTTGGCTA

361  AGAAAGCCCGAATAAGACCGCCCCATTTCCGGGTAGAGACGGAAAGAATATCCCGAAT
     ----+----|----+----|----+----|----+----|----+----|----+----|  420
     TCTTTCGGGCTTATTCTGGCGGGGTAAAGGCCCATCTCTGCCTTTCTTATAGGGCTTA

421  AGCAGGCGTTCGGGTTGCCCAGAGAGCCATCAGCAGTCCGGGTAAAAAGAAGAACATAAA
     ----+----|----+----|----+----|----+----|----+----|----+----|  480
     TCGTCCGCAAGCCCAACGGGTCCTCTCCGGTAGTCGTCAGGCCCATTTTTCTTCTTGTATTT

481  CAGCGCCCAGGTACGGCGTTTAAGGCGTTACGTGAGGAGAGGACGGTCATAGCGTCAGG
     ----+----|----+----|----+----|----+----|----+----|----+----|  540
     GTCGCGGGTCCATGCCGCAAATTCCGCAATGCACTCCTCCTGCCAGTATCGCAGTCC

541  CCAGAAAATAGAAGCGAGAGGTAAACATTAGCAAGCTTGTGTACATTTGTACATATCATC
     ----+----|----+----|----+----|----+----|----+----|----+----|  600
     GGTCTTTTATCTTCGCTCTCCATTTGTAATCGTTCGAACACATGTAAACATGTATAGTAG
```

FIG. 3b

```
601  GTCATACTTCATTGTGCAGACAGTTTTTACTGTCTGTTTTTCAGCGTAAGCGGCAGGCT
     ------+---------+---------+---------+---------+---------+   660
     CAGTATGAAGTAACACGTCTGTCAAAAATGACAGACAAAAAGTCGCATTCGCCGTCCGA

661  ACTATCGCCTGCATCCTGAATGAGATGTGGAACTCATCATGAAAGAAAATGCCGTAAGCG
     ------+---------+---------+---------+---------+---------+   720
     TGATAGCGGACGTAGGACTTACTCTACACCTTGAGTAGTACTTTCTTTTACGGCATTCGC

3'-AAGTCCGGTGTGACCTTCGCCATTTC-5'
721  CGCCAATGATCCTAAGCGACGGGAAAAATAATTCAGGCCACACTGGAAGCGGTAAAG
     ------+---------+---------+---------+---------+--------     778
     GCGGTTACTAGGATTCGCTGCCCTTTTTATTAAGTCCGGTGTGACCTTCGCCATTTC
                                            761 PRIMER
```

FIG. 3C

TEST  POSITIVE CONTROL  TEST  POSITIVE CONTROL
   
FIG. 6a  FIG. 6b

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
            (A) LENGTH: 755 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
CTTTACCGCT TCCAGTGTGG CCTGAAAACG CCATGCCGAC ACCAGCGCCC GCCAGCGTGC      60

CGAAACTGTA GAAACCATGC ATCATCGGCA GAACGGTTTT ATTCAGCTCG CGTTCGACCG     120

CCGCGCCTTC GACATTAATC GCCACTTCGG CGGCGCCAAA ACTGGCGCCG AAAACGGCTA     180

ATCCAAGGGC AAAAATCAGC GGCGAGGCGC ACCACAGCGC GACGCTAAGA ATAACCATCC     240

CGGTTACTGC ACAGGTCATC GTCGTGCGAA TAACCTTCCG GGTGCCAAAT CGTTTCACCA     300

GCCAGGCGGA ACAAAGAATA CCGCTCATTG AACCGATAGA AAGCCCGAAT AAGACCGCCC     360

CCATTTCCGC GGTAGAGACG GAAAGAATAT CCCGAATAGC AGGCGTTCGG GTTGCCCAGG     420

AGGCCATCAG CAGTCCGGGT AAAAAGAAGA ACATAAACAG CGCCCAGGTA CGGCGTTTTA     480

AGGCGTTACG TGAGGAGAGG ACGGTCATAG CGTCAGGCCA GAAAATAGAA GCGAGAGGTA     540

AACATTAGCA AGCTTGTGTA CATTTGTACA TATCATCGTC ATACTTCATT GTGCAGACAG     600

TTTTTACTGT CTGTTTTTTC AGCGTAAGCG GCAGGCTACT ATCGCCTGCA TCCTGAATGA     660

GATGTGGAAC TCATCATGAA AGAAAATGCC GTAAGCGCGC CAATGATCCT AAGCGACGGG     720

AAAAAATAAT TCAGGCCACA CTGGAAGCGG TAAAG                                755
```

(2) INFORMATION FOR SEQ ID NO:2:

(i) SEQUENCE CHARACTERISTICS:
            (A) LENGTH: 755 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: CONTROL COMPLEMENT (xi) SEQUENCE DESCRIPTION: SEQ ID NO:2:

```
CTTTACCGCT TCCAGTGTGG CCTGAATTAT TTTTTCCCGT CGCTTAGGAT CATTGGCGCG      60

CTTACGGCAT TTTCTTTCAT GATGAGTTCC ACATCTCATT CAGGATGCAG GCGATAGTAG     120

CCTGCCGCTT ACGCTGAAAA AACAGACAGT AAAAACTGTC TGCACAATGA AGTATGACGA     180

TGATATGTAC AAATGTACAC AAGCTTGCTA ATGTTTACCT CTCGCTTCTA TTTTCTGGCC     240

TGACGCTATG ACCGTCCTCT CCTCACGTAA CGCCTTAAAA CGCCGTACCT GGGCGCTGTT     300

TATGTTCTTC TTTTTACCCG GACTGCTGAT GGCCTCCTGG GCAACCCGAA CGCCTGCTAT     360

TCGGGATATT CTTTCCGTCT CTACCGCGGA AATGGGGGCG GTCTTATTCG GCTTTCTAT     420

CGGTTCAATG AGCGGTATTC TTTGTTCCGC CTGGCTGGTG AAACGATTTG GCACCCGGAA     480

GGTTATTCGC ACGACGATGA CCTGTGCAGT AACCGGGATG GTTATTCTTA GCGTCGCGCT     540

GTGGTGCGCC TCGCCGCTGA TTTTTGCCCT TGGATTAGCC GTTTTCGGCG CCAGTTTTGG     600
```

```
CGCCGCCGAA GTGGCGATTA ATGTCGAAGG CGCGGCGGTC GAACGCGAGC TGAATAAAAC      660

CGTTCTGCCG ATGATGCATG GTTTCTACAG TTTCGGCACG CTGGCGGGCG CTGGTGTCGG      720

CATGGCGTTT TCAGGCCACA CTGGAAGCGG TAAAG                                 755
```

(2) INFORMATION FOR SEQ ID NO:3:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
TAGCCGGGAC GCTTAATGCG GTTAACGCCA TGCCGACACC AGCGCCCGCC AGCGTGCCGA       60

AACTGTAGAA ACCATGCATC ATCGGCAGAA CGGTTTTATT CAGCTCGCGT TCGACCGCCG      120

CGCCTTCGAC ATTAATCGCC ACTTCGGCGG CGCCAAAACT GGCGCCGAAA ACGGCTAATC      180

CAAGGGCAAA AATCAGCGGC GAGGCGCACC ACAGCGCGAC GCTAAGAATA ACCATCCCGG      240

TTACTGCACA GGTCATCGTC GTGCGAATAA CCTTCCGGGT GCCAAATCGT TTCACCAGCC      300

AGGCGGAACA AAGAATACCG CTCATTGAAC CGATAGAAAG CCCGAATAAG ACCGCCCCCA      360

TTTCCGCGGT AGAGACGGAA AGAATATCCC GAATAGCAGG CGTTCGGGTT GCCCAGGAGG      420

CCATCAGCAG TCCGGGTAAA AGAAGAACA TAAACAGCGC CCAGGTACGG CGTTTTAAGG       480

CGTTACGTGA GGAGAGGACG GTCATAGCGT CAGGCCAGAA AATAGAAGCG AGAGGTAAAC      540

ATTAGCAAGC TTGTGTACAT TTGTACATAT CATCGTCATA CTTCATTGTG CAGACAGTTT      600

TTACTGTCTG TTTTTTCAGC GTAAGCGGCA GGCTACTATC GCCTGCATCC TGAATGAGAT      660

GTGGAACTCA TCATGAAAGA AAATGCCGTA AGCGCGCCAA TGATCCTAAG CGACGGGAAA      720

AAATAATTCA GGCCACACTG GAAGCGGTAA AG                                    752
```

(2) INFORMATION FOR SEQ ID NO:4:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: TARGET COMPLEMENT (xi) SEQUENCE DESCRIPTION: SEQ ID NO:4:

```
CTTTACCGCT TCCAGTGTGG CCTGAATTAT TTTTTCCCGT CGCTTAGGAT CATTGGCGCG       60

CTTACGGCAT TTTCTTTCAT GATGAGTTCC ACATCTCATT CAGGATGCAG GCGATAGTAG      120

CCTGCCGCTT ACGCTGAAAA AACAGACAGT AAAAACTGTC TGCACAATGA AGTATGACGA      180

TGATATGTAC AAATGTACAC AAGCTTGCTA ATGTTTACCT CTCGCTTCTA TTTTCTGGCC      240

TGACGCTATG ACCGTCCTCT CCTCACGTAA CGCCTTAAAA CGCCGTACCT GGGCGCTGTT      300
```

```
TATGTTCTTC TTTTTACCCG GACTGCTGAT GGCCTCCTGG GCAACCCGAA CGCCTGCTAT      360

TCGGGATATT CTTTCCGTCT CTACCGCGGA AATGGGGGCG GTCTTATTCG GGCTTTCTAT      420

CGGTTCAATG AGCGGTATTC TTTGTTCCGC CTGGCTGGTG AAACGATTTG GCACCCGGAA      480

GGTTATTCGC ACGACGATGA CCTGTGCAGT AACCGGGATG GTTATTCTTA GCGTCGCGCT      540

GTGGTGCGCC TCGCCGCTGA TTTTTGCCCT TGGATTAGCC GTTTTCGGCG CCAGTTTTGG      600

CGCCGCCGAA GTGGCGATTA ATGTCGAAGG CGCGGCGGTC GAACGCGAGC TGAATAAAAC      660

CGTTCTGCCG ATGATGCATG GTTTCTACAG TTTCGGCACG CTGGCGGGCG CTGGTGTCGG      720

CATGGCGTTA ACCGCATTAA GCGTCCCGGC TA                                    752
```

(2) INFORMATION FOR SEQ ID NO:5:

(i) SEQUENCE CHARACTERISTICS:
        (A) LENGTH: 778 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "SYNTHETIC"

(iii) HYPOTHETICAL: NO (iv) ANTI-SENSE: NO (xi) SEQUENCE DESCRIPTION: SEQ ID NO:5:

```
TAGCCGGGAC GCTTAATGCG GTTCTTTACC GCTTCCAGTG TGGCCTGAAA ACGCCATGCC       60

GACACCAGCG CCCGCCAGCG TGCCGAAACT GTAGAAACCA TGCATCATCG GCAGAACGGT      120

TTTATTCAGC TCGCGTTCGA CCGCCGCGCC TTCGACATTA ATCGCCACTT CGGCGGCGCC      180

AAAACTGGCG CCGAAAACGG CTAATCCAAG GGCAAAAATC AGCGGCGAGG CGCACCACAG      240

CGCGACGCTA AGAATAACCA TCCCGGTTAC TGCACAGGTC ATCGTCGTGC GAATAACCTT      300

CCGGGTGCCA AATCGTTTCA CCAGCCAGGC GGAACAAAGA ATACCGCTCA TTGAACCGAT      360

AGAAAGCCCG AATAAGACCG CCCCCATTTC CGCGGTAGAG ACGGAAAGAA TATCCCGAAT      420

AGCAGGCGTT CGGGTTGCCC AGGAGGCCAT CAGCAGTCCG GGTAAAAAGA AGAACATAAA      480

CAGCGCCCAG GTACGGCGTT TTAAGGCGTT ACGTGAGGAG AGGACGGTCA TAGCGTCAGG      540

CCAGAAAATA GAAGCGAGAG GTAAACATTA GCAAGCTTGT GTACATTTGT ACATATCATC      600

GTCATACTTC ATTGTGCAGA CAGTTTTTAC TGTCTGTTTT TTCAGCGTAA GCGGCAGGCT      660

ACTATCGCCT GCATCCTGAA TGAGATGTGG AACTCATCAT GAAAGAAAAT GCCGTAAGCG      720

CGCCAATGAT CCTAAGCGAC GGGAAAAAAT AATTCAGGCC ACACTGGAAG CGGTAAAG       778
```

(2) INFORMATION FOR SEQ ID NO:6:

(i) SEQUENCE CHARACTERISTICS:
        (A) LENGTH: 778 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AMPLICON COMPLEMENT (xi) SEQUENCE DESCRIPTION: SEQ ID NO:6:

```
CTTTACCGCT TCCAGTGTGG CCTGAATTAT TTTTTCCCGT CGCTTAGGAT CATTGGCGCG      60

CTTACGGCAT TTTCTTTCAT GATGAGTTCC ACATCTCATT CAGGATGCAG GCGATAGTAG     120

CCTGCCGCTT ACGCTGAAAA AACAGACAGT AAAAACTGTC TGCACAATGA AGTATGACGA     180

TGATATGTAC AAATGTACAC AAGCTTGCTA ATGTTTACCT CTCGCTTCTA TTTTCTGGCC     240

TGACGCTATG ACCGTCCTCT CCTCACGTAA CGCCTTAAAA CGCCGTACCT GGGCGCTGTT     300

TATGTTCTTC TTTTTACCCG GACTGCTGAT GGCCTCCTGG GCAACCCGAA CGCCTGCTAT     360

TCGGGATATT CTTTCCGTCT CTACCGCGGA AATGGGGGCG GTCTTATTCG GGCTTTCTAT     420

CGGTTCAATG AGCGGTATTC TTTGTTCCGC CTGGCTGGTG AAACGATTTG GCACCCGGAA     480

GGTTATTCGC ACGACGATGA CCTGTGCAGT AACCGGGATG GTTATTCTTA GCGTCGCGCT     540

GTGGTGCGCC TCGCCGCTGA TTTTTGCCCT TGGATTAGCC GTTTTCGGCG CCAGTTTTGG     600

CGCCGCCGAA GTGGCGATTA ATGTCGAAGG CGCGGCGGTC GAACGCGAGC TGAATAAAAC     660

CGTTCTGCCG ATGATGCATG GTTTCTACAG TTTCGGCACG CTGGCGGGCG CTGGTGTCGG     720

CATGGCGTTT TCAGGCCACA CTGGAAGCGG TAAAGAACCG CATTAAGCGT CCCGGCTA      778
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = " 761 PRIMER"

(iii) HYPOTHETICAL: NO (iv) ANTI-SENSE: NO (xi) SEQUENCE DESCRIPTION: SEQ ID NO:7:

```
CTTTACCGCT TCCAGTGTGG CCTGAA                                           26
```

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "761 PRIMER COMPLEMENT"

(xi) SEQUENCE DESCRIPTION: SEQ ID NO:8:

```
TTCAGGCCAC ACTGGAAGCG GTAAAG                                           26
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "35 PRIMER"

(iii) HYPOTHETICAL: NO (iv) ANTI-SENSE: NO

-continued (xi) SEQUENCE DESCRIPTION: SEQ ID NO:9:

TAGCCGGGAC GCTTAATGCG GTTAAC                26

METHOD FOR DETECTING BACTERIA USING PCR

CROSS REFERENCE TO RELATED APPLICATION

This application is a continuation-in-part of U.S. application Ser. No. 08/714,718, filed Sep. 19, 1996, now abandoned.

FIELD OF THE INVENTION

This invention relates to the field of molecular biology and particularly to a rapid method for detection of selected target bacteria. Specifically the target bacteria are detected in a homogeneous format by means of labeling DNA amplification products with a fluorescent dye where amplification proceeds in the presence of a control DNA to validate the amplification reaction.

BACKGROUND OF THE INVENTION

Detecting and identifying bacteria is important in various medical and public health contexts and is important in controlling the quality of the food chain. Innumerable protocols, proprietary apparatus and kits have evolved to meet the needs of the rapidly growing field of bacterial detection. These require highly trained and skilled personnel to carry out the necessary procedures and even more highly trained and skilled personnel to evaluate the results. Moreover, many of the existing tests are extremely sensitive to environmental factors, such as growth and storage conditions and the presence of and competition from other bacteria or microorganisms. This puts an even greater emphasis on the need for exacting procedures and highly skilled operatives. Tests of the prior art are often expensive both with regard to reagents and to the apparatus in which the tests are run. Additionally, these tests require confirmation since they often are not adequately selective or inclusive resulting in both false positive and false negative results.

Polymerase chain reaction (PCR) is a powerful analytical tool permitting the amplification of any desired specific nucleic acid sequence contained in a nucleic acid or mixture thereof. The use of this procedure for bacterial detection has been reported in the literature. However, as it is commonly practiced, it is a procedure which demands adherence to strict protocols under strict conditions and requires personnel of advanced skills and training in order to achieve a reliable result.

In all DNA based methods for detection of organisms, and particularly in the PCR test procedure, extraneous components that may enhance or inhibit the test reaction make obtaining creditable results difficult. This occurs in testing food-derived matrices for bacterial contaminants that effect quality such as pathogens, spoilage, and off-taste promoters and the like. Because the test results in such circumstances are critical, it is important to evaluate the effectiveness of any particular test. The invention provides a positive control which is useful in establishing test validity.

The test procedure of the invention is PCR-based. In U.S. Pat. No. 4,683,202, basic to that art, Mullis describes a procedure in which separate, complementary-strands of the nucleic acid are treated with a molar excess of two oligonucleotide primers and the primers are extended to form complementary primer extension products which act as templates for synthesizing the desired nucleic acid sequence. The steps of the reaction, a sequence of thermal treatments, are carried out stepwise or simultaneously and are repeated as often as desired. Typically as many as thirty-five or more cycles are necessary to obtain a number of replicas adequate for further processing.

In U.S. Pat. No. 4,683,195, Mullis et al. teach that a specific nucleic acid sequence may be cloned into a vector by using primers to amplify the sequence which contain restriction sites on their non-complementary ends and a nucleic acid fragment may be prepared from an existing shorter fragment using the amplification process.

PCR has several applications designed to detect the presence of a specific DNA sequence only by amplification. It would be extremely advantageous to include a control reaction in any such PCR test because, when a test is negative for a target, it is important to know if that result is true or if the reaction failed due to instrument malfunction or inhibition of the reaction due to sample matrix effects. The latter is particularly common in testing food samples to determine the presence of pathogens or other organisms harmful to product quality. Samples containing, for example, cocoa, a potent inhibitor of PCR, may well contain a pathogen that will be masked in an uncontrolled PCR-based test. A positive control replication composition and method is the subject of the instant invention.

Williams et al. in "DNA Polymorphisms Amplified by Arbitrary Primers are Useful as Genetic Markers", *Nucleic Acid Research*, Vol. 18, No. 22, p. 6531–6535 and Welsh et al., "Fingerprinting Genomes using PCR with Arbitrary Primers", *Nucleic Acid Research*, Vol. 18, No. 22, p. 7213–7218 both demonstrate the use of single, arbitrary primers in a DNA amplification reaction to generate a characteristic pattern of amplification products from genomic DNA from a variety of sources including bacteria. In WO93/11264, Jensen et al. teach the use of a single arbitrary primer across a broad spectrum of microorganisms. Control reactions are not addressed.

Shuldiner et al., in PB92-100932 NTIS, teach detecting an RNA sequence by tagging the sequence with a unique random nucleotide sequence during reverse transcription. The unique nucleotide sequence is then utilized to selectively amplify the resulting DNA sequence reducing the number of false positives obtained as a result of contaminating DNA such as from an endogenous source or from carry-over. This procedure lacks the control aspects of the instant invention which permit avoiding false negatives as well as false positives.

Tercero et al. (EP 586112), teach a vector useful as positive control in PCR amplification. The vector contains a sequence substantially identical to that of a primer used in the procedure which, after amplification, yields a product differing in size from that produced by the target. If only the vector is amplified the result is a true negative, but if neither vector nor target are amplified then the test must be faulty. Requisite in such a control protocol is some means to separate the different size products. Because the control and the target reactions are carried out in the same vessel and co-amplified, there are competing reactions that, in some circumstances reduce the sensitivity of the procedure. This results from preferential amplification of one of the targets. Also required are reference for size of product DNAs since in the case of only a single amplification product it must be determined whether it is test product or control product. Thus, the disclosure of Tercero et al. does not address homogeneous detection and is not adapted thereto.

In summary, the literature does not disclose a bacterial test method that 1) uses simplified molecular biology techniques that require no special skills in preparing and handling reagents and in carrying out the protocol, 2) is insensitive to environmental factors affecting phenotypic expression, and 3) is both selective and inclusive and has a positive control integrated into the protocol.

SUMMARY OF THE INVENTION

The present invention provides a method for the detection of a target bacteria in a complex sample mixture suspected of containing a target bacteria comprising:(i) obtaining total target bacteria DNA from said target bacteria;(ii) contacting said total target bacteria DNA with a test replication composition to form a first reaction mixture and a positive control replication composition to form a second reaction mixture, said test replication composition comprising: a) a polymerase; b) a primer pair consisting of a first primer and a second primer, each primer capable of hybridizing to a portion of said total target bacteria DNA; and c) reagents and buffers necessary for effecting DNA amplification; said positive control replication composition comprising: a) a polymerase; b) at least one control nucleic acid fragment; c) a single primer capable of hybridizing to a portion of said control nucleic acid fragment; and d) reagents and buffers necessary to effect DNA amplification;(iii) thermocycling the first and second reaction mixtures of step (ii) thereby producing DNA amplification products consisting of either or both; a) amplified total target bacteria DNA to produce multiple copies of target DNA; b) amplified control nucleic acid fragment; and (iv) detecting the amplification products of step (iii) wherein the presence of amplified control nucleic acid fragment alone indicates a successful reaction and wherein the presence of multiple copies of target DNA indicates the presence of the target bacteria in the complex mixture.

The detection methods of the present invention further encompass the detection of the target bacteria, and particularly pathogenic bacteria, by either gel electrophoresis or fluorescent means, the fluorescent means involving the use of DNA intercalating agents.

In another embodiment of the invention the target bacteria is detected from a complex mixture comprising background bacteria and food matrices.

BRIEF DESCRIPTION OF THE DRAWINGS

BIOLOGICAL DEPOSIT, AND SEQUENCE LISTING

FIGS. 1A–1C is a depiction of the Salmonella specific target DNA showing the primer binding sites for the 761 and 35 primers.

FIGS. 2A–2C is a depiction of the control DNA showing the primer binding sites for the 761 primer.

FIGS. 3A–3C is a depiction of the amplicon inserted into pUC18 to create the control plasmid.

Figure 4:
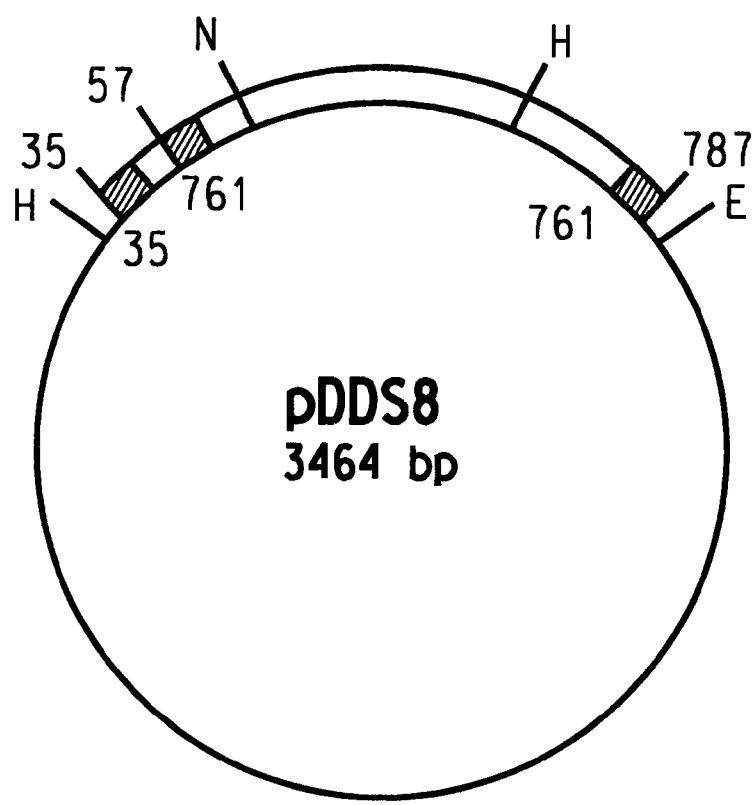

FIG. 4 is a plasmid map of the control pUC18 based plasmid, containing two 761 priming sites.

Figure 5A:
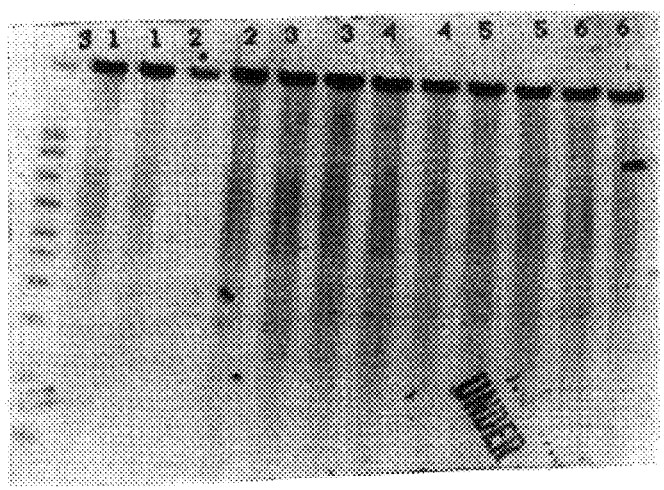

FIG. 5A is a gel analysis of clones s1–6 amplified with only the 761 primer.

Figure 5B:
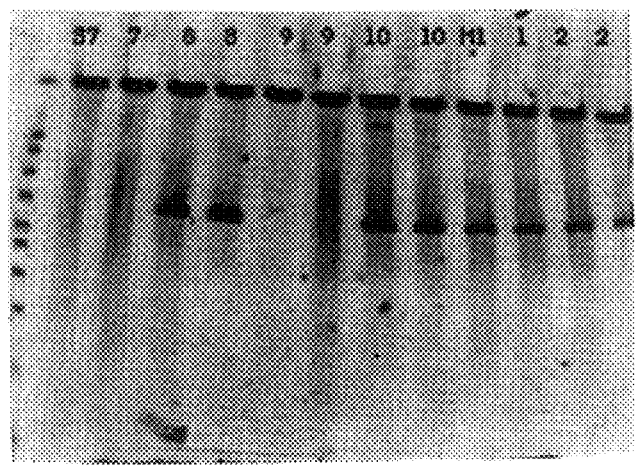

FIG. 5B is a gel analysis of clone s7–s10 and mixes m1–m2 amplified with only the 761 primer.

Figure 5C:
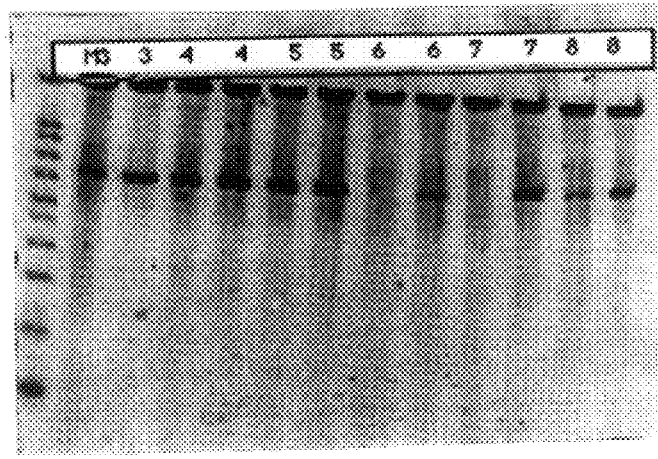

FIG. 5C is a gel analysis of control reactions with either the two primers 761 and 35 or with the 761 primer alone, showing that the product band in contrail reactions does not appear in the absence of the 35 primer.

FIG. 6A is a gel electrophoresis analysis of PCR products from replicate reactions using sample (test) tablets or using positive control tablets to detect Salmonella in a black pepper sample.

FIG. 6B is a gel electrophoresis analysis of PCR products from replicate reactions using sample (test) tablets or using positive control tablets to detect Salmonella in a yogurt sample.

Figure 7A:
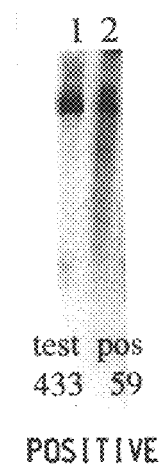

FIG. 7A shows a gel and homogeneous dye analysis of a positive PCR result for a Salmonella-spiked milk sample.

Figure 7B:
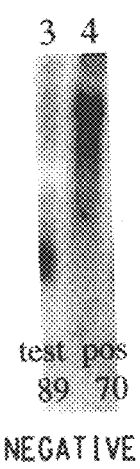

FIG. 7B shows a gel and homogeneous dye analysis of a negative PCR result for an unspiked milk sample.

Figure 7C:
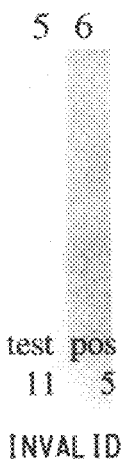

FIG. 7C shows a homogeneous dye analysis of an invalid PCR reaction.

Figure 8A:
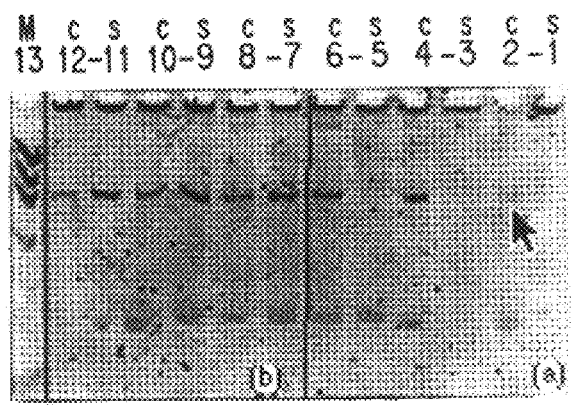

FIG. 8A is a gel analysis of PCR reactions of test (S) and control (c) reactions for unspiked (panel a) and *s. virchow* spiked (panel b) ground beef samples.

Figure 8B:
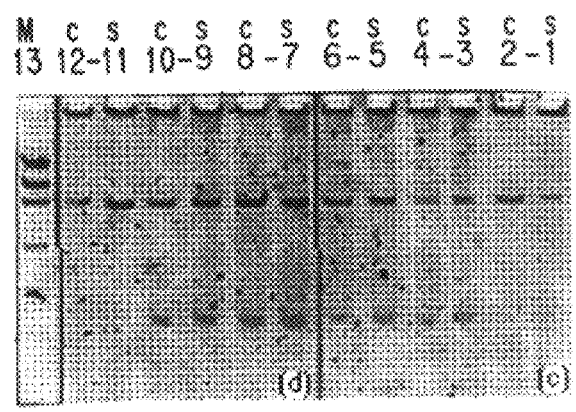

FIG. 8B is a gel analysis of PCR reactions of test (S) and control (c) reactions for *S. newport* (panel c) and *S. hadar* (panel d) spiked ground beef samples.

Figure 8C:
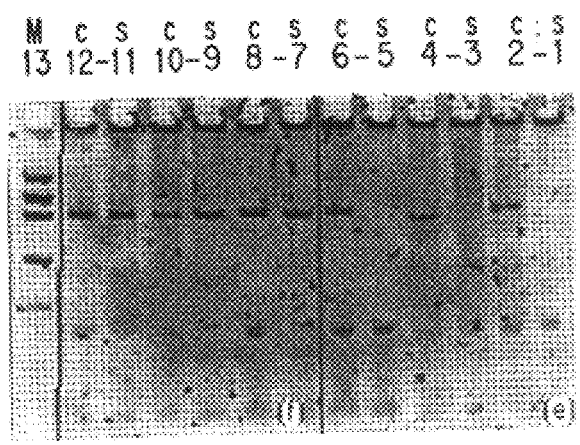

FIG. 8C is a gel analysis of PCR reactions of test (S) and control (c) reactions for unspiked (panel a) and *s. virchow* spiked (panel b) ground sausage samples.

Figure 8D:
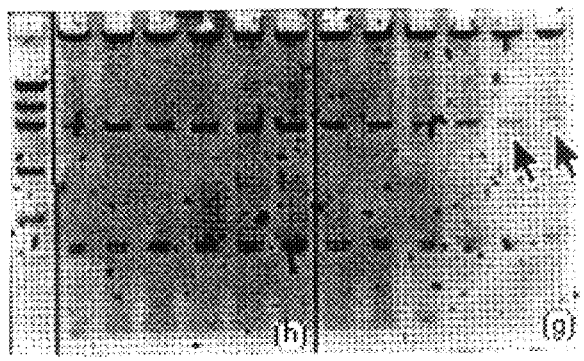

FIG. 8D is a gel analysis of PCR reactions of test (S) and control (c) reactions for *S. newport* (panel c) and *S. hadar* (panel d) spiked ground sausage samples.

Figure 8E:
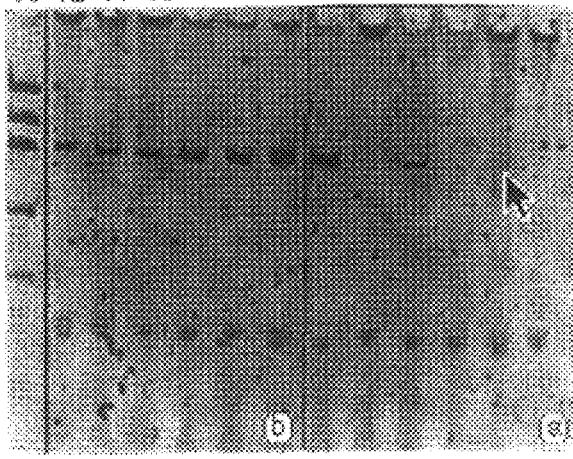

FIG. 8E is a gel analysis of PCR reactions of test (S) and control (c) reactions for unspiked (panel a) and *s. virchow* spiked (panel b) ground pork samples.

Figure 8F:
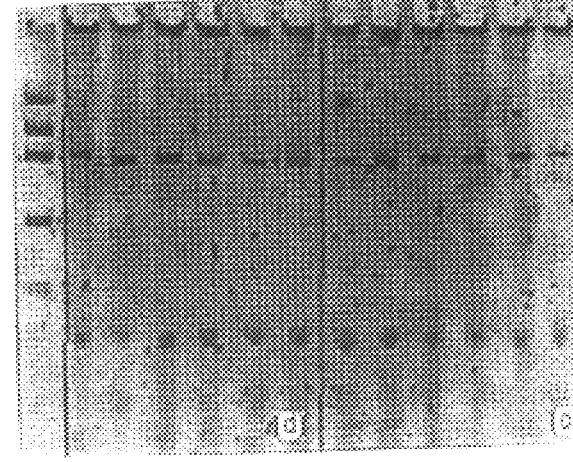

FIG. 8F is a gel analysis of PCR reactions of test (S) and control (c) reactions for *S. newport* (panel c) and *S. hadar* (panel d) spiked ground pork samples.

Figure 9:
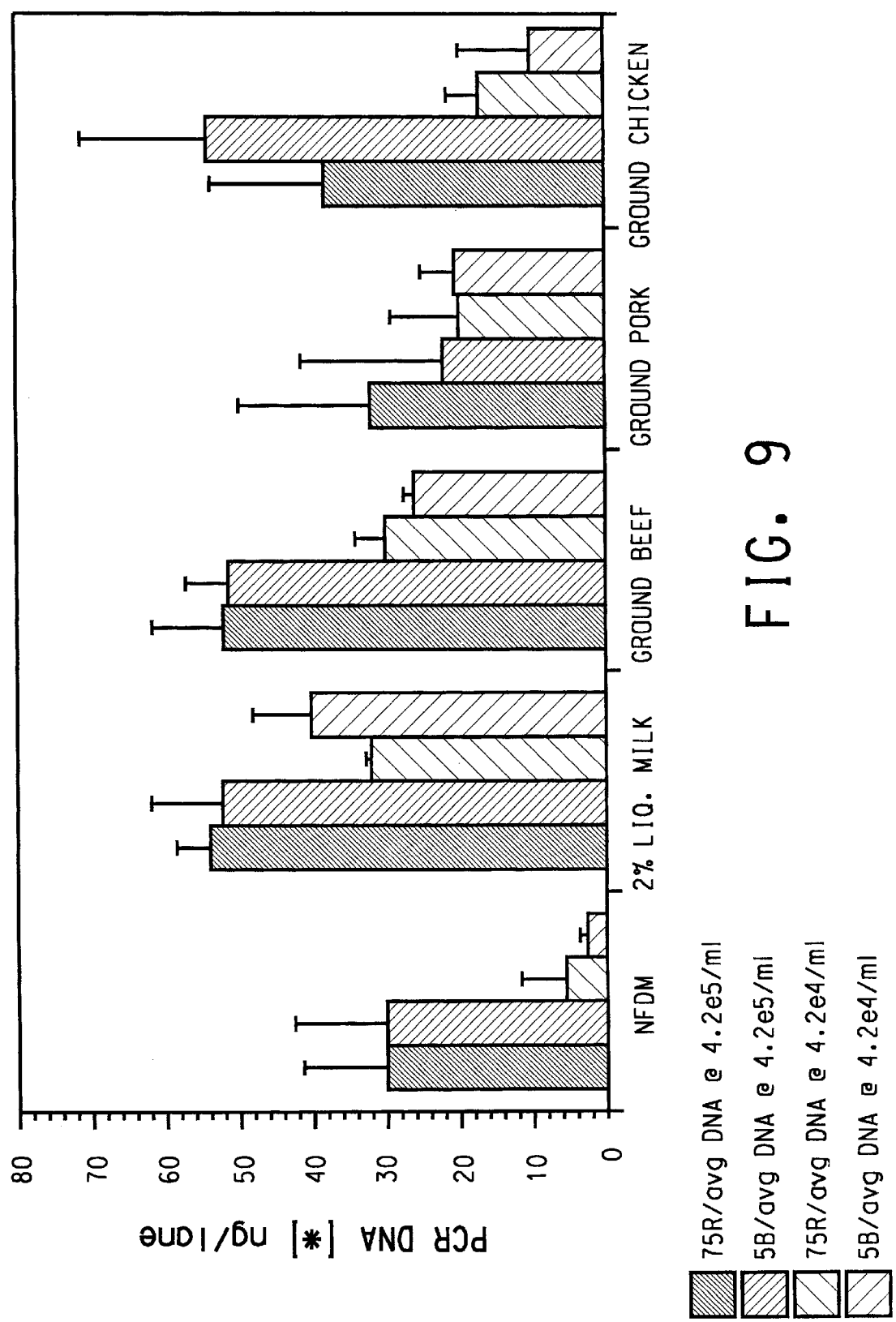

FIG. 9 represents the digital lysis of electrophoresis gel separation of amplification products from Salmonella from various food samples.

Applicants have made the following biological deposit under the terms of the Budapest Treaty on the International Recognition of the Deposit of Microorganisms for the Purposes of Patent Procedure:

| Depositor Identification Reference | Int'l. Depository Designation | Date of Deposit |
| --- | --- | --- |
| pUC 18 (carrying Salmonella Sequence SEQ ID NO:1) | | (expected September 19, 1996) |

Deposits were made at the American Type Culture Collection (ATCC) international depository located at 12301 Parklawn Drive, Rockville, Md. 20852 U.S.A.

Applicants have provided one sequence listing in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to OJ EPO, 12/1992.

SEQ ID NO: 1 is the nucleotide sequence of the control DNA having two 761 primer binding sites on the 3' and 5' ends.

SEQ ID NO: 2 is the complement of the nucleotide sequence of the control DNA having two 761 primer binding sites on the 3' and 5' ends.

SEQ ID NO:3 is the nucleotide sequence of the Salmonella specific target DNA having both 761 and 35 primer binding sites.

SEQ ID NO:4 is the complement of the nucleotide sequence of the Salmonella specific target DNA having both 761 and 35 primer binding sites.

SEQ ID NO:5 is the nucleic acid sequence of the DNA amplicon inserted into pUC18 included in the control tablet showing both the 35 and 761 primer binding sites.

SEQ ID NO:6 is the complement of the nucleic acid sequence of the DNA amplicon inserted into pUC18 included in the control tablet showing both the 35 and 761 primer binding sites.

SEQ ID NO:7 is the nucleotide sequence of the 761 primer, useful for the amplification of the control DNA and the Salmonella specific target.

SEQ ID NO:8 is the complement of the nucleotide sequence of the 761 primer, useful for the amplification of the control DNA and the Salmonella specific target.

SEQ ID NO: 9 is the nucleotide sequence of the 35 primer, useful for the amplification of the Salmonella specific target DNA.

DETAILED DESCRIPTION OF THE INVENTION

The following definitions are to be used to interpret the claims and specification.

When used herein "PCR" means the Polymerase Chain Reaction as described by Mullis et al. in U.S. Pat. No. 4,683,195 and Mullis in U.S. Pat. No. 4,683,202.

"BAM" means the FDA Bacteriological Analytical Manual published and distributed by the Association of Analytical Chemists Suite 400, 2200 Wilson Blvd, Arlington, Va. 22201-3301.

"BHI broth" means brain-heart infusion broth.

The term "complex sample mixture" will refer to a mixture of target and non-target bacteria in conjunction with any organic or inorganic material that will support the growth of a variety of microorganisms. The complex sample mixtures of the present invention comprise of a variety of different organic growth-supporting substances such as food matter, biological tissues, organic waste products, and the like.

The term "target bacteria" refers to the bacteria from which the target DNA is amplified. Target bacteria may be members of defined mixed cultures, or exist as contaminants in complex matrices. Target bacteria of particular interest are food-borne pathogens.

The term "non-target bacteria" will be used interchangeably with the term "background bacteria" and will refer to any bacteria that are found in the presence of the target bacteria but are not the target bacteria. Non-target bacteria may or may not be related genetically or biochemically to the target bacteria. Those non-target bacteria of most interest in the context of the present application are non-pathogenic food-borne bacteria.

The term "non-selective growth" or "non-selective enrichment" refers to the growth of target and non-target bacteria in a medium designed to resuscitate both target and non-target which have been injured or compromised by the sampling process. "Non-selective growth media" will refer to either a liquid or solid media designed to encourage the growth of both target and background bacteria. The non-selective growth media of the present invention is buffered to allow for the variations in pH of a variety of different food matrices.

"Nucleic acid" refers to a molecule which can be single-stranded or double-stranded, comprising monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The term "total target bacteria DNA" refers to any DNA contained within the target bacteria that contains a distinctive sequence by which the target bacteria may be identified. Total target bacteria DNA may include genomic DNA, episomal or plasmid DNA or cDNA derived from genomic DNA.

The term "target nucleic acid" or "target DNA" refers to a nucleic acid fragment that is detected by the present detection method and is indicative of the presence of a target bacterium. The target DNA is typically a unique portion of the target bacteria genome and specifically distinguishes the target bacteria from all other bacteria.

The term "amplification primer" or simply "primer" refers to a nucleic acid fragment or sequence that is complementary to at least one section along a strand of the target nucleic acid, wherein the purpose of the primer is to sponsor and direct nucleic acid replication of a portion of the target nucleic acid along that strand. Primers can be designed to be complementary to specific segments of a targeted sequence. In PCR, for example, each primer is used in combination with another primer forming a "primer set" or "primer pair"; this pair flanks the targeted sequence to be amplified. The term "primer", as such, is used generally by Applicants to encompass any sequence-binding oligonucleotide which functions to initiate the nucleic acid replication process.

The term "control nucleic acid fragment" refers to a fragment of DNA bounded on both the 5' and 3' ends with identical primer binding sites such that amplification of the control nucleic acid fragment may be accomplished with a single primer. The control nucleic acid fragment will typically be of a size and base composition similar to the target DNA to be detected. The control nucleic acid fragment may optionally reside as an insert in a plasmid or vector and may be incorporated into a tabletted reagent for the convenience of assay.

The term "replication composition" or "nucleic acid replication composition" refers to a composition comprising the ingredients necessary for performing nucleic acid amplification. Nucleic acid replication compositions may be provided in a variety of forms including liquid mixtures as well as tabletted reagents. If PCR methodology is selected, the replication composition would include, for example, nucleotide triphosphates, at least one primer with appropriate sequences, DNA polymerase, suitable buffers and proteins. A "test replication composition" refers to a composition specifically designed to amplify target DNA.

A "positive control replication composition" refers to a composition that will amplify a control nucleic acid fragment.

The term "tabletted reagent" will refer to a solid reagent useful for packaging the test and positive control replication compositions. A "test tablet" and a "control tablet" refer to tablets that contain the control and target replication compositions respectively. In all cases tabletted reagents contain a stabilizer, typically, trehalose.

The term "amplification product" refers to specific DNA fragments generated from any primer-directed nucleic acid amplification reaction. Amplification products will generally be double stranded DNA (dsDNA) and will be amenable to being bound by intercalating agents.

The term "primer directed nucleic acid amplification" or "primer-directed amplification" refers to any method known in the art wherein primers are used to sponsor replication of nucleic acid sequences in the linear or logarithmic amplification of nucleic acid molecules. Applicants contemplate that primer-directed amplification may be accomplished by any of several schemes known in this art, including but not limited to the polymerase chain reaction (PCR), ligase chain reaction (LCR) or strand-displacement amplification (SDA).

The term "intercalating agent" means a fluorescent agent capable of intercalating into nucleic acid molecules. The term "intercalating agent" will be used interchangeably with the term "intercalating dye". Intercalating agents emit a fluorescent signal when intercalated into the nucleic acid and will not generate any signal when not intercalated. Typical of intercalating agents are the cyanine dyes available from Molecular Probes, Inc. (Eugene, Oreg., USA).

The term "Fluorescent Intensity Units" will be abbreviated "FIU".

The term "homogeneous detection" refers to a method for the detection of DNA amplification products where no separation of products from template or primers is necessary. Homogeneous detection of the present invention is typically accomplished using an intercalating fluorescent dye capable of emitting a specific emission wavelength in response to an excitation wavelength of light. Homogeneous detection utilizing such dyes is referred to as detection by "fluorescent means".

Utility Statement

The present invention is a method for the detection of a specific target bacteria in a complex sample mixture. The sample mixture may contain a variety of components including non-target or background microorganisms as well as other organic contaminants such as food debris. The target bacteria of greatest interest are pathogenic bacteria commonly known to infect food such as Salmonella, Listeria, *E. coli* and Clostridia. The method proceeds by first culturing the complex sample mixture in a non-selective growth media to resuscitate the target bacteria. Next total target bacteria DNA is released and subjected to DNA amplification protocol with a primer pair selected to amplify a specific, identifying portion of the target bacteria DNA. A control DNA is amplified concurrently with the target bacteria target DNA. The control DNA is specifically designed to be amplified with a single primer that is identical to one of the primers used in the amplification of the target genomic DNA. Use of this control validates the amplification reaction. Detection of the amplified target DNA and the control is accomplished by gel electrophoresis or by fluorescent means. The present method is particularly useful when carried out in a homogeneous format where fluorescence emissions from dyes, incorporated in the amplification products, may be detected without the separation of products from primers or DNA templates.

The improvements of the present method using the control DNA over current techniques are clear and include the advantages that; (i) the control may be amplified using a single primer; (ii) the amount of the control amplification product is independent of any target DNA contained in the sample; (iii) the control DNA can be tabletted with other amplification reagents for ease of use and high degree of reproducibility in both manual and automated test procedures; (iv) the control can be used with homogeneous detection, i.e., without separation of product DNA from reactants and (v) use of the control avoids competing reactions by using separate test vessels for the suspected target and for the control.

Non-selective or pre-enrichment growth

Target bacteria of the present invention include any bacterium found to be a contaminant of food. Of greatest interest are pathogenic bacteria including, but not limited to members of the genera, Salmonella, Listeria, Escherichia, and Clostridia.

The minimum industry standard for the detection of food-borne bacterial pathogens is a method that will reliably detect the presence of one pathogen cell in 25 g of food matrix. In order to meet this stringent test enrichment methods and media have been developed to enhance the growth of the target pathogen cell in order to facilitate it's detection by biochemical, immunological or nucleic acid hybridization means. Typical enrichment procedures employ media that will not only enhance the growth and health of the target bacteria but will also promote the growth of any background or non-target microorganisms present. For example the U.S. Food and Drug Administration endorses a Salmonella assay procedure described in Andrews et al., "Isolation and Identification of Salmonella Species," Chapter 7 in Bacteriological Analytical Manual, 6th Edition, Association of Official Analytical Chemists, Arlington, Va. (1984). In this procedure the non-selective broth medium is used to restore injured Salmonella cells to a stable condition and to promote growth. Typical of such non-selective growth media is brain-heart infusion (BHI) broth, or lactose BHI broth, or simply lactose broth, both commercially available from a number of vendors including GIBCO/BRL (Gaithersburg, Md.) and DIFCO Laboratories (Detroit, Mich.). Non-selective media have been developed for a variety of bacterial pathogens and one of skill in the art will know to select a medium appropriate for the particular organism to be enriched. A general discussion and recipes of non-selective media are described in the Bacteriological Analytical Manual. (1984), supra.

After non-selective growth, a sample of the complex mixtures is removed for further analysis. This sampling procedure may be accomplished by a variety of means, however, it is preferred if retrieval is done using a perforated piece of Porex™ high density polyethylene. Porex™ is particularly suited for the sampling process as the small pore size of the polyethylene allows for maximum extraction of bacterial cells while excluding the large particles of food matrix. The retrieved, enriched bacterial sample is then lysed in a lysis buffer and subjected to a DNA amplification protocol in the presence of an internal DNA control.

Target DNA

Target DNA is any DNA that is specific to, and may be used to identify a particular target bacteria. A large number of sequences have been identified that are specific to various pathogenic bacteria. For the detection of pathogenic *E. coli* for example, Samapour (*J. Clin. Microbiol.* (1995), 33(8), 2150–4) teaches the detection of *E. coli* 0157:H7 by restriction fragment length polymorphism using Shiga-like toxin genes which are conserved between the 0157:H7 serotype and shigella. Similarly, Ramotar et al. (*J. Clin. Microbiol.* (1995), 33(3), 519–24) and Fratamico et al. (*J. Clin. Microbiol.* (1995), 33(8), 2188–91) teach PCR based methods for the detection of conserved 0157:H7 genes encoding either shiga-like toxins or verotoxins. Similar sequence have been identified for the detection of Listeria. In U.S. Pat. No. 5,523,205 and JP 05219997 DNA probes capable of hybridizing to a portion of the genome of pathogenic *Listeria monocytogenes*, are disclosed. DE 4238699 and EP 576842 teach methods for detection of *Listeria monocytogenes* using primers designed to give amplification products specific to the *monocytogenes* genome and EP 576842 describes amplification primers based on genes encoding the highly conserved iap (invasion-associated protein) of Listeria. Finally, WO 9500664; WO 9425597 and WO 9425595 all disclose sequences derived from the Salmonella genome useful for the specific detection and identification of Salmonella species.

It is within the scope of the present invention that any of the above mentioned sequences, specific to a particular bacterial pathogen may serve as the target sequence in the present detection method, depending on the organism to be detected. Of particular interest is the Salmonella specific target sequence given as SEQ ID NO's:3 and 4. The Salmonella target sequence was obtained by amplification of Salmonella genomic DNA using the primers 761 (SEQ ID NO:7) and 35 (SEQ ID NO:9). The Salmonella target sequence and the primer binding sites are shown in FIGS. 1A–C.

Construction Of Control Nucleic Acid Fragment

The control nucleic acid fragment or DNA of the invention is contained within a DNA vector based on pUC18 [Sambrook, J. et al., *Molecular Cloning: A Laboratory Manual*, Second Edition, Cold Spring Harbor Laboratory Press (1989)]. Control DNA will be of appropriate size and base composition to permit amplification by a method primer directed amplification. The control DNA may be isolated from the target bacteria, or from another source, but must be reproducibly amplified under the same conditions that permit the amplification of the target DNA. In a preferred embodiment, the control DNA is similar in size and base composition to the target DNA to be detected. For example, a control nucleic acid fragment was isolated from the genus Salmonella and was identical to the target to be detected, except that it was engineered to allow for amplification with a single primer (761; (SEQ ID NO:2). The control nucleic acid fragment used herein has the nucleotide sequence as given in SEQ ID NO's:1 and 2 and the location of the 761 primer binding sites is shown in FIGS. 2A–C. The control DNA amplicon inserted in pUC18 comprised a 761 primer binding site inserted at base 32 (see FIGS. 3A–C) to make an insert of 778 bases.

The control DNA is useful to validate the amplification reaction. Amplification of the control DNA is accomplished concurrently with the test sample containing the target DNA. Within the context of the present invention a sample is subjected to the test PCR procedure in parallel with a control containing the control DNA as well as the sample. If the control shows amplification, there is positive indication that the procedure has been effective regardless of the positive or negative results attained in the parallel test. In order to achieve significant validation of the amplification reaction a suitable number of copies of the control DNA must be included in each amplification reaction. Copies of control DNA per reaction may range from 10 copies to $1\times10^4$ copies where 100 copies to 1000 copies are preferred.

It is well known that sample matrix components, including food, can cause inhibition of PCR and therefore a resulting decrease in product formation and signal. Alternatively, the presence of certain food components in the PCR reaction have also been found to result in the opposite result, i.e. enhancement of the signal when fluorescent dye detection is employed. In non-homogeneous detection systems, such enhancement may not be noted and would not cause difficulty with analysis. However, in a homogeneous detection system, signal enhancement in the absence of a proper control could lead to false positive results. Use of the control as described herein eliminates such false positive results. Moreover, by calibrating the level of response in the control, it is possible to evaluate and compensate for any suppression or enhancement of the reaction in the test caused by extraneous material such as is found in many food-derived matrices.

Target Amplification

In order to identify a target by the present method, bacterial cells contained within a complex sample mixture and grown in a non-selective media are lysed in a lysis buffer to release total target bacteria DNA. DNA is then amplified according to a standard method for primer directed amplification. Typically, PCR is used and follows a standard thermocycling procedure in the presence of an appropriate nucleic acid replication composition. A suitable nucleic acid replication composition will contain for example, dATP, dCTP, dGTP, dTTP, target specific primers and a suitable polymerase. Primers will be selected to specifically amplify target DNA. If nucleic acid composition is in liquid form, suitable buffers known in the art are used. (Sambrook, J. et al., supra). Alternatively if the composition is contained in a tabletted reagent, then typical tabletting reagents are included such as stabilizers and the like. Within the context of the present invention replication compositions will be modified depending on whether they are designed to be used to amplify target DNA or the control DNA. Replication compositions that will amplify the target DNA, (test replication compositions) will include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) will include (i) a polymerase (generally thermostable) (ii) the control DNA; (iii) at least one primer capable of hybridizing to the control DNA; and (iv) necessary buffers for the amplification reaction to proceed. In some instances it may be useful to include a negative control replication composition. The negative control composition will contain the same reagents as the test composition but without the polymerase. The primary function of such a control is to monitor spurious background fluorescence in a homogeneous format when the method employs a fluorescent means of detection.

Replication compositions may be in either liquid or tabletted form where a tablet is preferred for ease of assay. Tablets are prepared according to the "snow gun" process, fully described in U.S. Pat. Nos. 5,307,640 (Fawzey et al.); 4,762,857 (Bollin, Jr. et al.); 4,678,812 (Bollin, Jr. et al.), 3,932,943 (Briggs et al.), and U.S. Pat. No. 5,475,984 (application Ser. No. 08/298,231) (Fermani et al.). In general, the control and test compositions are frozen into particles by means of a cryogenic liquid, the particles providing feedstock for tabletting.

The snow gun process uses a cryogenic liquid for producing frozen particles of a liquid product in a housing which comprises the steps of: (a) introducing the cryogenic liquid into the housing in an annular, downward direction creating a substantially continuous downwardly directed circumferential wall of cryogenic liquid, defining an interior entrapment zone; and (b) introducing droplets of the liquid product into the entrapment zone, whereby the cryogenic liquid freezes the liquid product droplets to produce frozen particles.

Detection Methods

Amplification products produced in the present method may be detected by any means known in the art where both gel electrophoresis and fluorescence detection are suitable. Methods of gel electrophoresis of DNA are common and well known in the art, and may be practiced according to a variety of protocols including those found in Southern, E. M et al., *Pulsed Field Gel Electrophoresis*. (1995), 1–19. Editor(s): Monaco, Anthony P. Publisher: IRL Press, Oxford, UK.

Where fluorescence detection is used, a fluorescent intercalating dye is employed to detect the presence of amplification products. The intercalating dye, as described below, may be added either before or after DNA amplification, depending on the properties of the dye. Excitation of control or test samples containing amplification products will result in a specific wave length emitted. Measurement and comparison of light emission from the control and test samples provide a means of determining the presence of amplification products.

Irrespective of the detection method used a positive result in the test well is always considered a positive result regardless of the result in the control well. A positive result in the control well, regardless of the test well result, affirms the functioning of the process. Negative results in both wells must be considered inconclusive. When using fluorescence detection, there may be some conditions where the test well reaction may be calibrated and correction made for the effects of fluorescence enhancement or suppression by extraneous matter from the original sample, such as is common with some foodstuffs.

Intercalating Agents For Fluorescence Detection

Where a fluorescent means of detection of DNA amplification products is used an intercalating agent capable of binding to double stranded DNA (dsDNA) and emitting a fluorescent signal is a preferred reagent. A variety of suitable intercalating agents are known in the art such as propidium iodide (PI) and ethidium bromide (EB) [Sailer et al., Cytometry (1996), 25(2), 164–172] Oxazole Yellow [EP 714986], TO-TO™ (1,1'-(4,4,7,7-tetramethyl-4,7-diazaundecamethylene)-bis-4-[3-methyl-2,3-dihydro-(benzo-1,3-thiazole)-2-methylidene]-quinolinium tetraiodide), a homodimer of thiazole orange [Axton et al., *Mol. Cell. Probes* (1994), 8(3), 245–50] oxazole orange (YOYO)[Srinivasan et al., *Appl. Theor. Electrophor.* (1993), 3(5), 235–9] as well as the cyanine dyes [U.S. Pat. No. 5,563,037]. Preferred in the present method are the unsymmetrical cyanine dyes such as are discussed in U.S. Pat. No. 5,563,037; U.S. Pat. No. 5,534,416; U.S. Pat. No. 5,321,130 and U.S. Pat. No. 5,436,134 hereby incorporated by reference.

Where it is preferred that the intercalating dye be added during or before the DNA amplification reaction a dye must be chosen that is both thermostable and will not inhibit the amplification reaction. Most suitable are the cyanine dyes YO-PRO-1™ (Quinolinium, 4-[(3-methyl-2(3H)-benzoxazolylidene)methyl]-1-[3-(trimethylammonio)propyl]-,diiodide) and syber green™ available from Molecular Probes, Inc. (Eugene, Oreg.). These dyes are particularly suited for use in the present invention due to their high extinction coefficient, near zero fluorescence when unbound to DNA, suitable binding affinity to double-stranded DNA and reasonable photostability. Further, both dyes are sufficiently resistant to the elevated processing temperatures at the time intervals used to provide an effective signal during the amplification reaction. Cyanine dyes which are particularly suited for use prior to or during DNA amplification generally will have binding constants from about from about $1 \times 10^4$ to about $5 \times 10^5$ (molar$^{-1}$).

Where interference with thermocyling is not an issue it is possible to expand the list of suitable intercalating agents to include those with binding constants higher than $5 \times 10^5$ (molar$^{-1}$). Intercalating agents with binding constants at this level are expected to interfere with the primer directed amplification and thus are not good candidates for addition to an amplification reaction during or prior to thermocycling. For example TO-TO-1™Quinolinium, 1,1'-[1,3-propanediylbis[(dimethyliminio)-3,1-propanediyl]]bis[4-[(3-methyl-2(3H)-benzothiazolylidene)methyl]]-, tetraiodide, will interfere with the DNA amplification reaction, but if added to the sample after amplification, it is a very serviceable fluorescent indicator.

As mentioned, the intercalating agent can be provided at any step of the method prior to fluorescence detection. For example, the intercalating agent may be present in either the test or control replication composition, may be added during thermocyling or may be added just prior to fluorescence detection. Typically the dye is added to the sample to give a final concentration of about 3 uM. Thermocycling proceeds according to typical cycling times and temperatures.

The intercalating agent chosen for use in the instant method may be temperature sensitive; i.e., the binding affinity of the intercalating agent for dsDNA and hence the magnitude of the fluorescent signal emitted may vary with temperature. Accordingly, it is readily apparent to one skilled in the art that instrument calibration, positive and negative controls and samples must all be assayed under controlled temperature conditions. Alternatively, a mathematical algorithm may be developed in order to compensate for variations in ambient and calibration temperatures. For example, the following algorithm comprises a simple linear multiplier that calculates the fluorescence value at a standard calibration temperature (FIUc) as a function of the ambient temperature at which sample measurements are taken (t) and the fluorescence intensity units (FIUt) recorded at that temperature:

FIUc=FIUt X(TCF), wherein

FIUc=the calculated fluorescence value;

FIUt=the measured fluorescence value at a given ambient temperature (t); and

TCF=((0.25+0.05(t))/1.45.

This algorithm produces a constant result over a temperature range of 15–35° C.

DESCRIPTION OF PREFERRED EMBODIMENTS

The method of the invention comprises three elements which are performed after conventional non-selective enrichment of a sample suspected to contain a target bacteria. The elements are (i) DNA preparation, (ii) PCR amplification using primers specific to the target bacteria, and (iii) use of a positive control. The primers anneal to and amplify only target-specific sequences, and detection is accomplished using a simple gel electrophoretic and staining procedure or alternatively by a fluorescent scheme. The complexity of using PCR has been simplified through the use of pre-mixed lysing reagents and tabletted PCR reagents including both a test tablet and a control tablet.

This invention also concerns the method of making and using a positive control replication composition comprising a control nucleic acid fragment in a pUC18 based plasmid, typically contained within a tabletted reagent. The control nucleic acid fragment is engineered so that it may be amplified using a single primer and the tabletted reagent typically includes a stabilizer such as trehalose. By using the positive control replication composition in parallel with a test replication composition, assurance is provided that the processing cycle was operative.

Typically the method proceeds as follows:

A complex sample mixture containing food debris and suspected of containing target bacteria is non-selectively enriched for at least 20 hrs according to BAM protocols. After enrichment the sample is diluted 1:10 in BHI broth. The diluted broth is then incubated for 3 hours at 37° C. A sample of the incubated culture is contacted with a lysis buffer at 95° C., lysing the cells and releasing total target bacteria DNA. Equal portions of the sample containing the lysed cells are aliquoted into 2 tubes, one containing a test tablet and the other containing a positive control tablet. The contents of the test and control tubes are then subjected to standard PCR thermocyling resulting in the production of amplification products. A typical thermocyling procedure is 2 min and 15 sec at 94° C. followed by 35 cycles of a 2 temperature protocol: 15 sec. at 94° C. and 3 min at 72° C. or 65° C. After the last cycle at 72° C. there is a 7 min holding period at 72° C.

Amplification products may be detected either by gel electrophoresis or by a fluorescent detection scheme. If using gel electrophoresis tracking dye is added to the thermocycled sample and aliquots are added to the gel and electrophoreised along side a graduated mass ladder on the gel. The graduated mass ladder is an aqueous based molecular weight marker solution comprising a mixture of different sized DNA markers and a tracking dye. A graduated mass ladder is electrophoresed on each gel and is instrumental in determining the size of the sample DNA to be detected and is also a measure of the sensitivity of the gel detection system.

Failure to detect the control product indicates a test failure for negative results in the test well. Failure to detect the control product with a positive test sample is considered a positive test for screening purposes. Such a case would likely be a result of a small degree of inhibition and a high level of target DNA in the test sample to produce sufficient product. Electrophoresis protocols other than PAGE may be adapted to this step as is well-known to those skilled in the art.

In a preferred embodiment the assay is performed in a homogeneous format and the detection process utilizes a fluorescent DNA intercalating dye added before the DNA amplification reaction. A complex sample mixture containing food debris and suspected of containing target bacteria is non-selectively enriched, and lysed as described above. Test and control replication compositions (typically in tabletted form) are added to the samples and primer directed DNA amplification (typically PCR) is performed. Contained within the test and control replication composition is the fluorescent intercalating dye. Preferred are asymmetrical cyanine dyes, capable of intercalating into the DNA molecule and having a binding constant of less than $5\times10^5$ (molar$^{-1}$). An example of such a dyes are YO-PRO-1™ (Quinolinium, 4-[(3-methyl-2(3H)-benzoxazolylidene) methyl]-1-[3-(trimethylammonio)propyl]-,diiodide) and syber green™ available from Molecular Probes, Inc. (Eugene, Oreg.). Preferred dyes fluoresce at a specific wavelength when intercalated in dsDNA and have no fluorescence in unbound form when subjected to an excitation wavelength. Upon completion of the DNA amplification reaction fluorescence is measured without the separation of amplification products from primers or templates. Fluorescence emissions are read on a standard fluorometer where the levels of fluorescence indicate the presence of amplification products.

Alternatively, amplification products may be detected by fluorescent means where the intercalating dye is added after the DNA amplification reaction. In such a method the test and control samples that have been subjected to thermocyling are separated into the wells of a microtiter plate and the intercalating dye is added. Resulting fluorescence emissions from the test and control wells give an indication of the presence of amplification products. Intercalating dyes in this mode of fluorescence detection need not have the low binding constants of those added prior to DNA amplification. For example, the cyanine dye TO-TO™ (1,1'-(4,4,7,7-tetramethyl-4,7-diazaundecamethylene)-bis-4-[3-methyl-2,3-dihydro-(benzo-1,3-thiazole)-2-methylidene]-quinolinium tetraiodide), having a binding constant greater than $5\times10^5$ (molar$^{-1}$) is particularly suitable.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Procedures for plasmid construction and manipulation as well as primer directed amplification are well known in the art. Techniques suitable for use in the following examples may be found in Sambrook, J. et al., Molecular Cloning: A Laboratory Manual, Second Edition, Cold Spring Harbor Laboratory Press (1989).

Materials and methods suitable for the maintenance and growth of bacterial cultures are well known in the art. Techniques suitable for use in the following examples may be found in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994) or Thomas D. Brock in Biotechnology: A Textbook of Industrial Microbiology, Second Edition (1989) Sinauer Associates, Inc., Sunderland, Mass. or Bacteriological Analytical Manual. 6th Edition, Association of Official Analytical Chemists, Arlington, Va. (1984).

The non-selective medium used in the following examples was lactose broth obtained from (DIFCO Laboratories (Detroit, Mich.).

Primers 761 (SEQ ID NO:7) and 35 (SEQ ID NO:9), were prepared by Research Genetics, Huntsville, Ala.

All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Composition of Tablets

| Composition Of Positive Control Tablet | | |
| --- | --- | --- |
| Trehalose | 90.15 | Weight % |
| Carbowax | 9.82 | Weight % |
| dNTP | 0.042 | Weight % |
| 761 Primer (SEQ ID NO:7) | 0.0013 | Weight % |
| control DNA (SEQ ID NO:1) | 10–10⁴ | copies |
| TAQ ® polymerase | 1.5–1.75 | U |
| Composition Of Test Tablet | | |
| Trehalose | 90.15 | Weight % |
| Carbowax | 9.82 | Weight % |
| dNTP | 0.042 | Weight % |
| 761 Primer (SEQ ID NO:7) | 0.0013 | Weight % |
| 35 Primer (SEQ ID NO:9) | 0.0013 | Weight % |
| Taq ® polymerase | 1.5–1.75 | U |
| Composition Of Negative Control Tablet | | |
| Trehalose | 90.15 | Weight % |
| Carbowax | 9.82 | Weight % |
| dNTP | 0.042 | Weight % |
| 761 Primer (SEQ ID NO:7) | 0.0013 | Weight % |
| 35 Primer (SEQ ID NO:9) | 0.0013 | Weight % |

Gel Electrophoresis Reagents

Molecular weight markers for gel electrophoresis detection of amplification products is provided as a graduated mass ladder having the following components:

Water (CAS No. 7732-18-5), 96.6276 Weight %;

Polyepichlorohydrin (CAS No. 26837-85-8, 2,5 Weight % available as "FICOLL, Type 400-DL" from Sigma Chemical Company, Dorset, England;

Tris (CAS No. 77-86-1) 0.54 Weight % available from Fisher Scientific;

Boric Acid (CAS No. 10043-35-3) 0.27%;

Ethylenediaminetetra-acidic Acid (EDTA)(CAS No. 60-00-4) 0.029 Weight %;

Xylene Cyanol FF (CAS No. 2650-17-1) 0.016 Weight %;

Sodium Dodecylsulfate (SDS)(CAS No. 151-21-3) 0.016 Weight %; and

6 DNA molecular weight marker fragments, 0.0014 Weight % from Life Technologies, Incorporated, Gaithersburg, Md.

Tracking dye used in the PAGE separation is composed of the following reagents:

Water 84.61 Weight %;
FICOLL 15.0 Weight %;
EDTA 0.19 Weight %; SDS 0.1 Weight %;
Xylene Cyanol FF 0.1 Weight %; and
EDTA 0.19 Weight % available from E. I. du Pont de Nemours and Company, Wilmington, Del. 19898.

Example 1

Construction of Control Plasmid

Cloning of Salmonella Target DNA

Example 1 was run to construct a control DNA plasmid, as shown in FIG. 4, by cloning a Salmonella typhimurium PCR product. The specific object was to clone 0.7 kb PCR product into the SmaI site of pUC18, then insert the complement of 761 (761c) primer sequence near 5' end (35 end) of the cloned fragment. This was facilitated by the location of the HpaI site at the 5' end of the insert. In this way the final product could be amplified with a single 761 primer to generate a near full length product.

Procedural steps were as follows:
i) linearized pUC18 with SmaI
ii) gel purified PCR product DNA generated by amplification with both 35 and 761 primers.
iii) ligated above and transformed DH5a
iv) Purified plasmids from hosts
v) restricted resulting plasmid with HpaI
vi) annealed 761c (SEQ ID NO:8) with 761 (SEQ ID NO:7)
vii) ligated the products of v and vi
viii) transformed DH5a with the ligation products of vii and selected for clones amplified with 761 primer alone.

pUC18 was prepared using 5 uL pUC18 DNA (Life Technologies Inc.), 2 uL React 4 buffer (Life Technologies Inc.), 11 uL H₂O and 2 uL SmaI (Life Technologies Incorporated). The 20 uL mixture was heated for 2 h at 37° C. Then 4 uL of 50 mmn EDTA was added. The procedure was repeated and the two digestions were pooled. 4 uL of the resultant product was gel analyzed as follows:

i) ran 20 uL/lane on acrylamide gel
ii) cut out band on transilluminator
iii) chopped up piece in 1.5 mL tube with pipette tip
iv) incubated at 4° C. overnight in TE buffer (approximately 20 h)
v) spun through a 0.65 um Ultrafree cartridge (Millipore)
vi) Ethanol precipitated
vii) analyzed on acrylamide gel Three ligations were made:
1. pUC18 SmaI+unpurified PCR product
2. puc18 SmaI+purified product
3. puc18 SmaI These were composed as listed below:

| #1 | #2 | #3 |
| --- | --- | --- |
| 1 uL puc18 SmaI | 1 uL puc18 SmaI | 1 uL puc18 SmaI |
| 1 uL unpurified prod | 1 uL purified prod | — |
| 2 uL 5x buffer | 2 uL 5x buffer | 2 uL 5x buffer |
| 5 uL dH₂O | 5 uL H₂O | 6 uL 5x H₂O |
| 1 uL Ligase | 1 uL Ligase | 1 uL Ligase |

The three 10 uL aliquots were incubated for 4 h at 15° C. and transformations were prepared in E. coli DH5a and analyzed on plates as listed below:

| TRANSFORMATIONS |
| --- |
| i) 3 uL Ligation #1 |
| ii) 3 uL Ligation #2 |
| iii) 3 uL Ligation #3 |
| iv) 5 uL Control puc18 plasmid |
| v) no DNA |
| vi) unligated pUC18 SmaI |
| PLATES |
| 100 ug/mL Ampicillin (50 mg/mL stock) |
| 50 uL x-Gal (20 mg/mL) |
| 4 uL IPTG (200 mg/mL) |

Seven colonies were picked from ampicillin 100 ug/mL plates of transformation ii) to check for inserts. These were all white or faint blue colonies. A Hind III digest was carried out. Wizard™ minipreps (Promega Corp 7113 Benhart Dr, Raleigh, N.C.) of the seven colonies were prepared according to the Promega directions and 5 uL of each was cut with Hind III. The result was that all clones apparently were the same size indicating no inserts as confirmed by agarose gel electrophoresis. Thus, additional screening was done.

Thirty six colonies were picked from a pooled and replated group of colonies and transferred to a fresh plate and screened for amplification products using both 761 (SEQ ID NO:7) and 35 (SEA ID NO:9) primers. Amplification products were detected in clones T12 and T 18 which were subjected to further analysis.

Analysis was done by EcoRI/Hind III digests. 5 uL each of minipreps (Wizard™ miniprep, Promega) was cut with EcoRI and Hind III in React 2 buffer. These were checked for insert on 1% agarose gel using as a marker Biomarker Low (BioVentures). The electrophoresis was about 1 h at 100 volts. Proper sized inserts, as confirmed by agarose gel electrophoresis were seen in both clones corresponding to a Hind III site at 581 bp as predicted.

Cloning of Target Specific Priming Sites 761.

The 761 (SEQ ID NO:7) priming site was cloned into T12. Annealed 761 (SEQ ID NO:7) and 761c (SEQ ID NO:8) (complement of 761) were inserted into the Hpa I site at 23 bp in the insert DNA.

The following steps were carried out in sequence:

i) Digest T12 with HpaI
ii) Dephosphorylate above
iii) Anneal primer 761 with 761c
iv) Ligate vector T12 with annealed primers
vi) Transform DH5a selecting for ampicillin resistance
vii) Screen for inserts of primer by amplification with 761 primer only The digests composition of T12 with HpaI were:

| T12 |
|---|
| 34 ul DNA |
| 4 uL 10x buffer |
| 2 uL HpaI |

These were held at 37° C. for 3 h.

T12 was gel separated and was used in ligation as follows. Primers were prepared by mixing primer 761 with its complement, 25 uL each at 0.05 ug/uL, then heating at 94° C. for 2 min followed by a ramp to 37° C. over 30 min, then an 8 minute to 4° C. in a Perkin Elmer cycler:

| CONTROL | TEST |
|---|---|
| 2 uL T12 HpaI | 2 uL T12 HpaI |
| 2 uL 5x Buffer | 2 uL 5x buffer |
|  | 1 uL annealed primer |
|  | (⅕x dilution) |
| 5 uL H$_2$O | 4 uL H$_2$O |
| 1 uL Ligase | 1 uL Ligase |

These were held at 15° C. for 4 h.

Three uL of each ligation was used to transform DH5a selecting for ampicilin resistance and loss of b-galactosidase activity. Ten colonies were picked from the test ligation and the remainder of the plate was pooled into 10 mixes. Lysates from all samples were amplified using only 761 primer. Also amplified were T12 vector and negative and positive controls. Included were amplifications with two primer tablets of T12 and negative and positive control DNAs. The results are shown in FIGS. 5A, B, and C. S1 to S10 in FIGS. 5A and 5B are single colony isolates. FIG. 5C shows controls. S8 and S10 were positive for a single 761 primer amplification as were all of the mixes.

Example 2

Preparation of Tabletted Reagents

Example 2 describes the preparation of the positive control and test PCR reagent tablets for the detection of target DNA.

Positive Control Tablet Formulation

The positive control tablet contained the following elements:

| REAGENT | QUANTITY/TABLET | QUANTITY/LOT (50,000 tablets) |
|---|---|---|
| deoxy nucleotides (25.0 mM) | 0.32 uL | 16.0 mL |
| primer 761 (20.0 um) | 0.09 uL | 4.5 mL |
| control DNA | 0.02 uL | 1.0 mL |
|  | (app. 10$^4$ copies) |  |
| Taq ® polymerase | 1.5 units | 75,000 units |
| trehalose | 6.608 mg | 330.4 g |
| carbowax | 0.72 m | 36 g |

Preparation of Positive Control PCR Tablet

1. The trehalose dihydrate and carbowax were dissolved in 750 mL of autoclaved deionized water.

2. The deoxy nucleotides, primer, control DNA, and Taq® polymerase were added to the solution.

3. The solution was adjusted to the final weight of 1357 g with autoclaved deionized water.

4. The solution was filtered through a 5 um cartridge.

5. The solution was then processed generally according to the teachings of U.S. Pat. No. 5,307,640 (Fawzy et al.) as improved in U.S. Pat. No. 5,475,984, a process dubbed a "snow-gun process." The solution was sprayed into a liquid nitrogen chamber at a reagent spray rate of 125 mL/min.

6. The frozen blend was collected in the tray at the end of the chamber due to gravity.

7. The frozen blend was then freeze-dried in a freeze drier (such as the GT6, available from Finn Aqua of Germany). The freeze drying program consisted of primary drying at a product temperature of −40° C. and a chamber pressure of 50 micron for 50 h. Secondary drying was done at 25° C. for 20 h.

8. The freeze dried blend was then sized through a 30 mesh screen.

9. The sized blend was then tabletted using a 3/32 inch tool.

Test Tablet Formulation

The test tablet contained the following elements:

| REAGENT | QUANTITY/TABLET | QUANTITY/LOT (50,000 tablets) |
|---|---|---|
| deoxy nucleotides (25.0 mM) | 0.32 uL | 16.0 mL |
| primer 761 (10 um) | 0.10 uL | 5.0 mL |
| primer 35 (10 um) | 0.10 uL | 5.0 mL |

-continued

| REAGENT | QUANTITY/TABLET | QUANTITY/LOT (50,000 tablets) |
|---|---|---|
| Taq ® polymerase | 1.5 units | 75,000 units |
| trehalose | 6.608 mg | 330.4 g |
| carbowax | 0.72 mg | 36.0 g |

Preparation of Test PCR Tablet

1. The trehalose dihydrate and carbowax were dissolved in 750 mL of autoclaved deionized water.

2. The deoxy nucleotides, primer and Taq® polymerase were added to the solution.

3. The solution was adjusted to the final weight of 1357 g with autoclaved deionized water.

4. The solution was filtered through a 5 um cartridge.

5. The solution was then processed generally according to the "snow gun" process as above. The solution was sprayed into a liquid nitrogen chamber at a reagent spray rate of 125 mL/min.

6. The frozen blend was collected in the tray at the end of the chamber due to gravity.

7. The frozen blend was then freeze-dried in a freeze drier (such as GT6 available from Finn-Aqua of Germany). The freeze drying program consisted of primary drying at a product temperature of −40° C. and a chamber pressure of 50 micron for 50 h. Secondary drying was done at 25° C. for 20 h.

8. The freeze dried blend was then sized through a 30 mesh screen.

9. The sized blend was then tabletted using using a 3/32 inch tooling.

Example 3

Identification of Salmonella from Spiked Food Sample

Example 3 illustrates the detection of Salmonella bacteria in food samples spiked with a specific concentration of Salmonella using the tabletted reagents as prepared in Example 2. After the introduction of Salmonella the food samples were incubated in a non-selective pre-enrichment medium for enhancement of bacterial titers.

Assay for Salmonella in Food Matrix Following Non-Selective Growth

1. Black pepper and frozen yogurt samples were non-selectively enriched by standard methods (BAM-FDA)

2. Following incubation a portion of the non-selective enrichment was spiked with Salmonella typhimurium at a concentration of $10^4$ cells per mL.

3. One mL portions of the spiked and unspiked non-selective enrichment were added to separate 15 mL screw cap tubes containing 9 mL of brain heart infusion broth (BHI).

4. The tubes were incubated at 37° C. for 3 h.

5. Five microliter volumes were removed from each tube and added to 195 microliters of lysis reagent (10 mM Tris-HCl, 28 mM KCl and 3 mM $MgCl_2$, pH=8.3 containing 0.25 mg of proteinase K per mL and 0.1% Triton X-100) in 2 mL screw-cap tubes. The tubes were incubated at 37° C. for 20 min, then 95° C. for 10 min.

6. Fifty microliter portions of each lysate sample prepared above were used to hydrate PCR test tablets and PCR positive control tablets (Example 2).

7. Both reaction tubes were therrnocycled under the following conditions:

| | |
|---|---|
| a. 94° C., 2 min | 1 cycle |
| b. 94° C., 15 sec<br>65° C., 1.5 min<br>72° C., 0.5 min | 35 cycles |
| c. 72° C., 7 min | 1 cycle |
| d. 4° C. and held at this temperature until used. | |

8. Following the thermocycling of the samples, the amplified products were separated by gel electrophoresis on a 4% polyacrylamide gel (29:1). The electrophoresis was run using a 0.5× TBE buffer (45 mM Tris-base, 45 mM Boric Acid and 1 mM EDTA) at a constant voltage of 100 volts for 30 min.

9. The separated DNA bands (see FIGS. 6A and 6B showing replicated tests) were stained in a solution of ethidium bromide 0.1 ug/mL) for 15 min. and then visualized by placing the gel on a UV transilluminator (such as a FOTO UV 300 available from Fotodyne, Inc., New Berlin, Wis.).

10. A determination of whether the sample contained Salmonella was made based on the following criteria:

a. A band corresponding to 750 bp in both sample and control lanes—indicating that the sample was positive for Salmonella.

b. No band in the sample lane and a band corresponding to 750 bp in the control lane—indicating that the sample was negative for Salmonella.

c. A band in the sample lane and no band on the control lane—in this instance, the PCR reaction is compromised due to a presumed matrix effect such that the typical $10^4$ CFU/mL sensitivity representative of the control reaction was not achieved. The positive result in the test lane indicates that the sample contained Salmonella at a higher concentration than the sensitivity limit of $10^4$ CFU/rrL. Result indicated that the sample was positive for Salmonella.

d. No band corresponding to 750 bp in either the sample lane or the control lane—no result can be reported. Due to either a chemical or mechanical (including thermal) abnormality the PCR process was compromised such that a sample containing $10^4$ CFU/nL would not have been sufficiently amplified to be detected.

Analysis of the bands shown in FIGS. 6A and 6B revealed that the 750 bp band was present in the sample lane and control lanes demonstrating that the sample was positive for the organism.

Example 4

Use of Control Plasmid in Homogeneous Detection of Salmonella

A test was run to demonstrate the utility of the control, in tablet form, for homogeneous detection. Homogenates of two foods, cocoa powder and powdered whole milk, were prepared by mixing 25 g of these foods with 225 ml of lactose broth medium. The homogenates were in some cases spiked with *Salmonella typhimurium* at approximately 100 cells per mL. All homogenates were incubated approximately 20 h at 37° C. after which samples of the foods were prepared for PCR by lysing the bacteria in a solution of proteinase K (0.25 mg/ml), triton X-100 (0.01%) and PCR buffer, described above by heating at 37° C. for 20 min. and then at 95° C. for 10 min. Next, 50 uL aliquots of the lysates were placed in tubes containing either test PCR tablets or control PCR tablets prepared as described above. These were subjected to thermocycling according to the following protocol:

| | | |
|---|---|---|
| a. 94° C., 2 min | | 1 cycle |
| b. 94° C., 15 sec | | 35 cycles |
| 65° C., 1.5 min | | |
| 72° C., 0.5 min | | |
| c. 72° C., 7 min | | 1 cycle |
| d. 4° C. and held at this temperature until used. | | |

Following cycling, 5 uL portions of the reactions were analyzed by polyacrylamide gel electrophoresis (PAGE).

Also, the same samples were analyzed by homogeneous detection as follows. To 45 uL of reactions, 5 uL of a 20 micromolar TO-TO-1 dye (obtained from Molecular Probes, Inc., Eugene, Oreg.) was added, then incubated for 5 min at room temperature. Fluorescent measurements of the mixtures was accomplished using a fluorimeter with excitation wavelength of 513 nm and emission wavelength of 533 nm. The fluorescence (in arbitrary fluorescence intensity units) was above the threshold level of 50 and therefore the test was valid for the milk samples. The fact that the test tablet amplification gave a fluorescence of 358 which is significantly greater than the control fluorescence indicates a positive test result. This is verified by the presence of the DNA product shown by the gel electrophoresis, as can be seen, and is an accurate result since this sample was spiked with *Salmonella typhimurium*.

FIGS. 7A–7C shows the results of the gel electrophoresis and homogeneous detection of the PCR reactions. Lanes 1 and 2 demonstrate a valid test with a positive result. In lane 2 the presence of a DNA band and fluorescence (in arbitrary fluorescence intensity units) above the pre-determined threshold level of 50 indicates an uninhibited positive control for the milk samples. The fact that the test tablet amplification gave a DNA band (lane 1) and fluorescence of 358 which is significantly greater than the control fluorescence indicates a positive test result for the presence of Salmonella. Lanes 3 and 4 demonstrate a valid test with a negative result. The fluorescence of the positive control (lane 4) was above the threshold level of 50 and therefore the test was valid. The test tablet fluorescence, however, was much lower than the corresponding spiked sample in lane 1 indicating a negative test result. Again this was verified by the absence of a specific DNA product band on the gel and was a correct result since this sample did not contain Salmonella. Finally, lanes 5 and 6 demonstrate an invalid test for cocoa powder. The positive control tablet (lane 6) gave a fluorescence of 5 which is well below the threshold of 50 and, therefore, the test is considered invalid. The accuracy of the homogeneous detection is again verified by the absence of DNA bands in lanes 5 and 6. These reactions were inhibited by the presence of cocoa powder, so no conclusion could be drawn concerning the presence or absence of Salmonella.

Example 5

Evaluation of PAGE Based Definitive Detection Process

Example 5 was run to establish threshold sensitivity according to the following:

Salmonella strains 1256 (*S. virchow*), 1261 (*S. newport*), and 1231 (*S. hadar*) were spiked into samples of ground beef, sausage, and ground pork purchased in a supermarket at a level of about $10^4$/mL. This was done after the samples had been suitably prepared and subjected to a standard BAM twenty-four hour pre-enrichment procedure. This was followed by a 1/10 dilution and grow back in the original flask in BHI at 37° C. for 3 h, lysis, hydration of a PCR test tablet and a PCR positive control tablet, thermalcycling. Triplicate sets of test and control reaction were performed for each food/inoculant combination. PAGE based analysis followed. The aliquots were as follows:

| FIG. | Panel | Sample | Innoculant |
|---|---|---|---|
| 8A | (a) | Ground Beef [gb] | -- Negative Control |
| 8A | (b) | [gb] | -- + 1256 (*S. virchow*) |
| 8B | (c) | [gb] | -- + 1261 (*S. newport*) |
| 8B | (d) | [gb] | -- + 1231 (*S. hadar*) |
| 8C | (e) | Sausage [gs] | -- Negative Control |
| 8C | (f) | [gs] | -- + 1256 (*S. virchow*) |
| 8D | (g) | [gs] | -- + 1261 (*S. newport*) |
| 8D | (h) | [gs] | -- + 1231 (*S. hadar*) |
| 8E | (i) | Ground Pork | -- Negative Control |
| 8E | (j) | [gp] | -- + 1256 (*S. virchow*) |
| 8F | (k) | [gp] | -- + 1261 (*S. newport*) |
| 8F | (l) | [gp] | -- + 1231 (*S. hadar*) |

The results are shown in FIGS. 8a–f. Arrows denote positive bands. Applicants concluded that the threshold sensitivity for these organisms is about $10^4$.

This was supported by a series of tests using the same method on the following: non-fat dried milk, 2 percent milk, ground beef, ground pork and ground chicken. Two lots of test reagents were used with only small differences in the results. Testing was done by spiking pre-enriched (BAM) samples at $10^4$ and $10^5$ cfu/nml with *S. typhimurium*. Results are shown in FIG. 9 for digital image analysis of each PCR reaction from tests of the spiked foods. The reaction products were separated by gel electrophoresis and each band intensity was quatified by comparison to DNA standards. A $10^4$ threshold appears adequate for all these food matrices.

We claim:

1. A method for the detection of a target bacteria in a complex sample mixture suspected of containing a target bacteria comprising:
   (i) obtaining total target bacteria DNA from said target bacteria;
   (ii) contacting said total target bacteria DNA with a test replication composition to form a first reaction mixture and a positive control replication composition to form a second reaction mixture, said test replication composition comprising:
      a) a polymerase
      b) a primer pair consisting of a first primer and a second primer, each primer capable of hybridizing to a portion of said total target bacteria DNA;
      c) reagents and buffers necessary to effect DNA amplification;
   said postive control replication composition comprising:
      a) a polymerase
      b) at least one control nucleic acid fragment
      c) a single primer capable of hybridizing to a portion of said control nucleic acid fragment
      d) reagents and buffers necessary to effect DNA amplification;
   (iii) thermocycling the first and second reaction mixtures of step (ii) thereby producing DNA amplification products consisting of either or both:
      a) amplified total target bacteria DNA to produce multiple copies of target DNA or
      b) amplified control nucleic acid fragment; and
   (iv) detecting the amplification products of step (iii) wherein the presence of amplified control nucleic acid fragment alone indicates a successful reaction and wherein the presence of multiple copies of target DNA indicates the presence of the target bacteria in the complex mixture.

2. The method according to claim 1 wherein said target bacteria is a pathogenic bacteria.

3. The method according to claim 2 wherein said pathogenic bacteria is selected from the group consisting of Salmonella, Listeria, Escherichia, and *clostridia*.

4. The method according to claim 1 wherein said complex mixture comprises a non-selectively enriched food matrix.

5. The method according to claim 1 wherein said test replication composition is provided in a tablet.

6. The method according to claim 1 wherein said positive control replication composition is provided in a tablet.

7. The method according to claim 1 wherein the presence of said amplification products is detected by fluorescent means.

8. The method according to claim 1, 5 or 6 wherein said test replication composition and said positive control replication composition comprise an intercalating agent.

9. The method according to claim 8 wherein said intercalating agent is an asymmetrical cyanine dye.

10. The method according to claim 1 wherein said first primer is a 761 primer having the sequence as set forth in SEQ ID NO: 7.

11. The method of claim 1 wherein said second primer is a 35 primer having the sequence as set forth in SEQ ID NO: 9.

12. The method according to claim 1 wherein said single primer is the same as either said first or said second primer.

13. The method according to claim 1 wherein said control nucleic acid fragment is a portion of the Salmonella genome having the nucleotide sequence as set forth in SEQ ID NO:1.

14. The method according to claim 1 wherein the number of said control nucleic acid fragments is from 1 to 10.

15. The method according to claim 1 wherein said detecting of amplification products is accomplished by gel electrophoresis.

16. The method according to claim 1 where in said detection of amplification products is accomplished by fluorescence means.

17. A control nucleic acid fragment useful as a control DNA to monitor the success of a DNA amplification reaction having the nucleotide sequence as set forth in SEQ ID NO:1.

18. The method according to claim 9 wherein said cyanine dye is selected from the group consisting of TO-TO-1™, Quinolinium, 1,1'-[1,3-propanediylbis[(dimethyliminio)-3,1-propanediyl]]bis[4-[(3-methyl-2(3H)-benzothiazolylidene)methyl]]-,tetraiodide, and YO-PRO-1™, Quinolinium, 4-[(3-methyl-2(3H)-benzoxazolylidene)methyl]-1-[3-(trimethylammonio)propyl]-,diiodide.

* * * * *